United States Patent

Ofner et al.

[11] Patent Number: 5,935,951
[45] Date of Patent: *Aug. 10, 1999

[54] 1-ACYL-4-ALIPHATYLAMINOPIPERIDINE COMPOUNDS

[75] Inventors: Silvio Ofner, Münchenstein; Siem Jacob Veenstra, Basel, both of Switzerland

[73] Assignee: Novartis Finance Corporation, New York, N.Y.

[*] Notice: This patent issued on a continued prosecution application filed under 37 CFR 1.53(d), and is subject to the twenty year patent term provisions of 35 U.S.C. 154(a)(2).

[21] Appl. No.: 08/809,277

[22] PCT Filed: Sep. 19, 1995

[86] PCT No.: PCT/EP95/03681

§ 371 Date: Mar. 5, 1997

§ 102(e) Date: Mar. 5, 1997

[87] PCT Pub. No.: WO96/10562

PCT Pub. Date: Apr. 11, 1996

[30] Foreign Application Priority Data

Sep. 30, 1994 [CH] Switzerland ............................. 2966/94

[51] Int. Cl.$^6$ .......................... A61K 31/54; A61K 31/43; C07D 417/60; C07D 211/08

[52] U.S. Cl. ..................................... 514/227.8; 514/231.5; 514/255; 514/311; 514/312; 514/330; 544/60; 544/129; 544/360; 546/192; 546/196; 546/204; 546/208; 546/209; 546/212; 546/213; 546/216; 546/219; 546/220; 546/278.4; 546/278.7

[58] Field of Search ..................... 546/192, 196, 546/207, 208, 209, 212, 213, 216, 219, 220, 278.4, 278.7; 514/311, 312, 330, 331, 329, 227.8, 231.5, 258; 544/60, 129, 360

[56] References Cited

U.S. PATENT DOCUMENTS 5,310,743  5/1994  Schilling et al. ........................ 514/311
5,459,270 10/1995  Williams et al. ..................... 546/278.7

FOREIGN PATENT DOCUMENTS 330461  8/1989  European Pat. Off. .
528495  2/1993  European Pat. Off. .
532456  3/1993  European Pat. Off. .
9511895  5/1995  WIPO .

OTHER PUBLICATIONS

Schilling et al. Chemical abstract vol. 119 No. 271005 "Prep of 1-acylpiperdation and their use as substance of P Antagonists" 1993.

*Primary Examiner*—John Kight
*Assistant Examiner*—Raymond Covington
*Attorney, Agent, or Firm*—Gregory D. Ferraro

[57] ABSTRACT

The invention relates to novel 1-acyl-4-aliphatylaminopiperidine compounds of

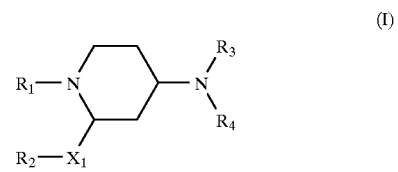

(I)

formula (I), in which $R_1$ is a benzoyl, naphthoyl or cycloalkanoyl radical which is unsubstituted or substituted by lower alkyl, lower alkoxy, halogen and/or trifluoromethyl; $R_2$ is cycloalkyl or a phenyl or naphthyl radical which is unsubstituted or substituted by lower alkyl, lower alkoxy, halogen, nitro, cyano and/or trifluoromethyl; $R_3$ and $R_4$ together are lower alkylene or aza-, oxa- or thia-lower alkylene; or $R_3$ is lower alkyl, lower alkoxy-lower alky, di-lower alkylamino-lower alkyl or a radical of the formula $—(CH_2)_n—C(=O)—R_5$ (Ia); and $R_4$ is hydrogen, lower alkyl or a radical of the formula $—(CH_2)_n—C(=O)—R_5$ (Ia); $R_5$ is (i) hydrogen, alkyl or alkyl which is substituted by halogen, lower alkoxy amino or amino substituted by lower alkyl, amino-lower alkyl, mono- or di-lower alkylaminoalkyl, lower alkanoyl, lower alkoxycarbonyl or lower alkylene or aza-, oxa- or thia-lower alkylene, (ii) hydroxyl, cycloalkoxy, lower alkoxy or lower alkoxy which is substituted by lower alkoxy, amino or amino substituted by lower alkyl, amino-lower alkyl, mono- or di-lower alkylamino-alkyl, lower alkanoyl, lower alkoxycarbonyl or lower alkylene or aza-, oxa- or thia-lower alkylene, or (iii) amino or amino substituted by lower alkyl, cycloalkyl, amino-lower alkyl, mono- or di-lower alkylaminoalkyl, lower alkanoyl, lower alkoxycarbonyl or lower alkylene or aza-, oxa- or thia-lower alkylene; $X_1$ is methylene, ethylene, a direct bond; a free or ketalized carbonyl group or a free or etherified hydroxymethylene group and n is 0 or 1, and their salts, processes for the preparation of the compounds according to the invention, pharmaceutical compositions containing these and their use as pharmaceutical active ingredients.

16 Claims, No Drawings

1-ACYL-4-ALIPHATYLAMINOPIPERIDINE COMPOUNDS

This is a 371 of PCT/EP95/03681, filed Sep. 19, 1995.

The invention relates to novel 1-acyl-4-aliphatylaminopiperidine compounds of the formula I

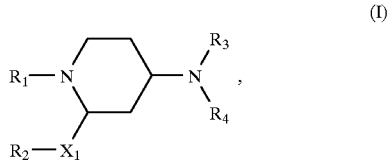

in which

R$_1$ is a benzoyl, naphthoyl or cycloalkanoyl radical which is unsubstituted or substituted by lower alkyl, lower alkoxy, halogen and/or trifluoromethyl;

R$_2$ is cycloalkyl or a phenyl or naphthyl radical which is unsubstituted or substituted by lower alkyl, lower alkoxy, halogen, nitro, cyano and/or trifluoromethyl;

R$_3$ and R$_4$ together are lower alkylene or aza, oxa- or thia-lower alkylene; or R$_3$ is lower alkyl, lower alkoxy-lower alkyl, di-lower alkylamino-lower alkyl or a radical of the formula —(CH$_2$)$_n$—(=O)—R$_5$ (Ia); and R$_4$ is hydrogen, lower alkyl or a radical of the formula —(CH$_2$)$_n$—C(=O)—R$_5$ (Ia);

R$_5$ is (i) hydrogen, alkyl or alkyl which is substituted by halogen, lower alkoxy, amino or amino substituted by lower alkyl, amino-lower alkyl, mono- or di-lower alkylaminoalkyl, lower alkanoyl, lower alkoxearbonyl or lower alkylene or aza-, oxa- or thia-lower alkylene, (ii) hydroxyl, cycloalkoxy, lower alkoxy or lower alkoxy which is substituted by lower alkoxy, amino or amino substituted by lower alkyl, amino-lower alkyl, mono- or di-lower alkylamino-alkyl, lower alkanoyl, lower alkoxycarbonyl or lower alkylene or aza-, oxa- or thia-lower alkylene, or (iii) amino or amino substituted by lower alkyl, cycloalkyl, amino-lower alkyl, mono- or di-lower alkylaminoalkyl, lower alkanoyl, lower alkoxycarbonyl or lower alkylene or aza-, oxa- or thia-lower alkylene;

X$_1$ is methylene, ethylene, a direct bond, a free or ketalized carbonyl group or a free or etherified hydorowcymethylene group; and n is 0 or 1, and their salts, with the exception of the compound (2R*,4S*)-N-[1-(3,5-bistrifluoromethyl-benzoyl)-2-(4-nitrobenzyl)-piperidin-4-yl]acetamide; process for the preparation of the compounds according to the invention, pharmaceutical preparations containing these, and their use as pharmaceutical active ingredients.

Cycloalkyl and radicals derived therefrom have, for example, 3 to 8, in particular 5 to 7, primarily 5 or 6, ring members and are, for example, cyclopentyl, cyclohexyl or cycloheptyl.

Alkyl which is substituted by halogen, lower alkoxy, amino or amino substituted by lower alkyl, amino-lower alkyl, mono- or di-lower alkylaminoalkyl, lower alkanoyl, lower alkoxycarbonyl or lower alkylene or aza-, oxa-, or thia-lower alkylene is, for example, haloalkyl, in particular halo-lower alkyl, lower alkoxyalkyl, in particular lower alkoxy-lower alkyl, aminoalkyl, in particular amino-lower alkyl, mono- or di-lower alkylaminoalkyl, in particular mono- or di-lower alkylamino-lower alkyl, lower alkanoylaminoalkyl, in particular lower alkanoylamino-lower alkyl, lower alkoxycarbonylaminoalkyl, in particular lower alkoxycarbonylamino-lower alkyl, pyrrolidinoalkyl, in particular pyrrolidino-lower alkyl, piperidinoalkyl, in particular piperidino-lower alkyl, free or N'-lower alkylated or N'-lower alkanoylated piperazinoalkyl, in particular the corresponding piperazino-lower alkyl, morpholino alkyl, in particular morpholino-lower alkyl, or free or S-oxidized thiomorpholinoalkyl, in particular the corresponding thiomorpholino-lower alkyl.

Amino substituted by lower alkyl, (3- to 8-membered) cycloalkyl, amino-lower alkyl, mono- or di-lower alkylaminoalkyl, lower alkanoyl, lower alkoxycarbonyl or lower alkylene or aza-, oxa- or thia-lower alkylene is, for example, mono- or di-lower alkylamino, (3- to 8-membered) cycloalkylamino, amino-lower alkylamino, mono- or di-lower alkylamino-lower alkylamino, lower alkanoylamino, lower-alkoxycarbonylamino, pyrrolidino, piperidino, free or N'-lower alkylated or N'-lower alkanoylated piperazino, morpholino or free or S-oxidized thiomorpholino.

Lower alkoxy which is substituted by lower alkoxy, amino or amino substituted by lower alkyl, amino-lower alkyl, mono- or di-lower alkylaminoalkyl, lower alkanoyl, lower alkoxycarbonyl or lower alkylene or aza-, oxa- or thia-lower alkylene is, for example, lower alkoxy-lower alkoxy, amino-lower alkoxy, mono- or di-lower alkylamino-lower alkoxy, lower alkanoylamino-lower alkoxy, lower alkoxycarbonylamino-lower alkoxy, pyrrolidino-lower alkoxy, piperidino-lower alkoxy, free or N'-lower alkylated or N'-lower alkanoylated piperazino-lower alkoxy, morpholino-lower alkoxy, or free or S-oxidized thiomorpholino-lower alkoxy.

Alkyl is, for example, straight-chain or branched C$_1$–C$_{14}$-alkyl, in particular C$_1$–C$_{10}$-alkyl, preferably lower alkyl.

Free or ketalized carbonyl is, for example, carbonyl or di-lower alkoxymethylene.

Etherified hydroxymethylene is, for example, lower alkoxymethylene.

Free or N'-lower alkylated or N'-lower alkanoylated piperazino-lower alkoxy is, for example, piperazino-lower alkoxy, N'-lower alkylpiperazino-lower alkoxy or N'-lower alkanoylpiperazino-lower alkoxy.

Free or N'-lower alkylated or N'-lower alkanoylated piperazino-lower alkyl is, for example, piperazino-lower alkyl, N'-lower alkylpiperazino-lower alkyl or N'-lower alkanoylpiperazino-lower alkyl.

The general definitions used above and below, if not defined differently, have the following meanings:

The expression "lower" means that corresponding groups or compounds each have up to and including 7, preferably up to and including 4, carbon atoms.

Lower alkyl is, for example, C$_1$–C$_7$alkyl, preferably C$_1$–C$_4$alkyl, such as, in particular, methyl or secondarily ethyl, propyl, isopropyl or butyl, but can also be isobutyl, secondary butyl, tertiary butyl or a C$_5$–C$_7$alkyl group, such as a pentyl, hexyl or heptyl group.

Lower alkoxy is, for example C$_1$–C$_7$alkoxy, preferably C$_1$–C$_4$alkoxy, such as methoxy, ethoxy, propoxy, isopropoxy or butoxy, but can also be isobutoxy, secondary butoxy, tertiary butoxy or a pentoxy, hexyloxy or heptyloxy group.

Halogen is, for example, chlorine or iodine, but can also be fluorine or bromine.

Lower alkylene or aza-, oxa- or thia-lower alkylene is, for example, 4- to 6-membered and is, for example, $C_4$–$C_6$alkylene or 3-aza-, 3-oxa- or 3-thia-$C_4$–$C_6$alkylene. Amino substituted by lower alkylene or aza-, oxa- or thia-lower alkylene, the group —$N(R_3)(R_4)$, is preferably pyrrolidino, piperidino, morpholino or free or S-oxidized thiomorpholino.

Lower alkoxy-lower alkyl carries the terminal lower alkoxy group preferably in a higher position than the α-position and is, for example, $C_1$–$C_7$alkoxy-$C_2$–$C_4$alkyl, preferably $C_1$–$C_4$alkoxy-$C_2$–$C_4$alkyl, such as 2-methoxyethyl, 2-ethoxyethyl, 3-methoxypropyl, 3-ethoxypropyl, 4-methoxybutyl or 4-ethoxybutyl.

Amino-lower alkyl is, for example, amino-$C_1$–$C_7$alkyl, preferably amino-$C_1$–$C_4$alkyl, such as aminomethyl, 2-aminoethyl, 3-aminopropyl or 4-aminobutyl.

Mono- or di-lower alkylamino-lower alkyl is, for example, mono- or di-$C_1$–$C_4$alkylamino-$C_1$–$C_4$alkyl, such as methylamino- or dimethylamino-$C_1$–$C_4$alkyl, ethylamino- or diethylamino-$C_1$–$C_4$alkyl, N-ethyl-N-methylamino-$C_1$–$C_4$alkyl, propylamino- or dipropylamino-$C_1$–$C_4$alkyl, diisopropylamino-$C_1$–$C_4$alkyl or dibutylamino-$C_1$–$C_4$alkyl, $C_1$–$C_4$alkyl being, for example, methyl, ethyl, propyl or butyl.

Lower alkanoyl is, for example, $C_1$–$C_7$alkanoyl, preferably $C_1$–$C_4$alkanoyl, such as formyl, acetyl, propionyl or butyryl, but can also be valeroyl, pivaloyl or caproyl.

Lower alkoxycarbonyl is, for example, $C_1$–$C_7$alkoxycarbonyl, preferably $C_1$–$C_4$alkoxycarbonyl, such as methoxycarbonyl, ethoxycarbonyl, propoxycarbonyl, isopropoxycarbonyl or butoxycarbonyl, but can also be Isobutoxycarbonyl, secondary butoxycarbonyl, tertiary butoxycarbonyl or a pentoxycarbonyl, hexyloxycarbonyl or heptyloxycarbonyl group.

Di-lower alkoxymethylene is, for example, di-$C_1$–$C_4$alkoxymethylene, such as dimethoxymethylene, diethoxymethylene, dipropoxymethylene or dibutoxymethylene.

Lower alkoxymethylene is, for example, $C_1$–$C_4$alkoxymethylene, such as methoxymethylene, ethoxymethylene, propoxymethylene or butoxymethylene.

Amino-lower alkoxy is, for example, amino-$C_1$–$C_7$alkoxy, preferably amino-$C_2$–$C_4$alkoxy, such as 2-aminoethoxy, 3-aminopropoxy or 4-aminobutoxy.

Di-lower alkylamino is, for example, di-$C_1$–$C_4$alkylamino, such as dimethylamino, diethylamino, N-ethyl-N-methylamino, dipropylamino, diisopropylamino or dibutylamino.

Free or oxidized thiomorpholino is, for example, thiomorpholino, S-oxythiomorpholino or S,S-dioxythiomorpholino.

Halo-lower alkyl is, for example, halo-, dihalo- or, in particular, trihalo-$C_1$–$C_4$alkyl, such as, in particular, trifluoromethyl or secondarily trifluoroethyl or trifluoropropyl.

Morpholino-lower alkoxy is, for example, morpholino-$C_1$–$C_4$alkoxy, such as morpholinomethoxy or 2-morpholinoethoxy, 3-morpholinopropoxy or 4-morpholinobutoxy.

Morpholino-lower alkyl is, for example, morpholino-$C_1$–$C_4$alkyl, such as morpholinomethyl oder 2-morpholinoethyl, 3-morpholinopropyl or 4-morpholinobutyl.

N-Mono- or N,N-di-lower alkylamino-lower alkoxy is, for example, N-mono- or N,N-di-$C_1$–$C_4$alkylamino-$C_1$–$C_4$alkoxy, such as methylamino- or dimethylamino-$C_1$–$C_4$alkoxy, ethylamino- or diethylamino-$C_1$–$C_4$alkoxy, N-ethyl-N-methylamino-$C_1$–$C_4$alkoxy, propylamino- or dipropylamino-$C_1$–$C_4$alkoxy, diisopropylamino-$C_1$–$C_4$alkoxy or butylamino-$C_1$–$C_4$alkoxy, $C_1$–$C_4$alkoxy being, for example, methoxy, ethoxy, propoxy or butoxy.

N'-Lower alkanoylpiperazino-lower alkoxy is, for example, N'-$C_1$–$C_7$alkanoyl-, such as N'-acetylpiperazino-$C_1$–$C_4$alkoxy, $C_1$–$C_4$alkoxy being, for example, methoxy, ethoxy, propoxy or butoxy.

N'-Lower alkylpiperazino-lower alkoxy is, for example, N'-$C_1$–$C_7$alkyl-, such as N'-methylpiperazino-$C_1$–$C_4$alkoxy, $C_1$–$C_4$alkoxy being, for example, methoxy, ethoxy, propoxy or butoxy.

N'-Lower alkanoylpiperazino-lower alkyl is, for example, N'-$C_1$–$C_7$alkanoyl-, such as N'-acetylpiperazino-$C_1$–$C_4$alkyl, $C_1$–$C_4$alkyl being, for example, methyl, ethyl, propyl or butyl.

N'-Lower alkylpiperazino-lower alkyl is, for example, N'-$C_1$–$C_7$alkyl-, such as N'-methylpiperazino-$C_1$–$C_4$alkyl, $C_1$–$C_4$alkyl being, for example, methyl, ethyl, propyl or butyl.

Lower alkanoylamino-lower alkoxy is, for example, $C_1$–$C_7$alkanoylamino-$C_1$–$C_4$alkoxy, preferably $C_1$–$C_4$alkanoylamino-$C_2$–$C_4$alkoxy, such as formylamino-$C_2$–$C_4$alkoxy, acetylamino-$C_2$–$C_4$alkoxy, propionylamino-$C_2$–$C_4$alkoxy or butyrylamino-$C_2$–$C_4$alkoxy, $C_2$–$C_4$alkoxy being, for example, ethoxy, propoxy, isopropoxy or butoxy.

Lower alkanoylamino-lower alkyl is, for example, $C_1$–$C_7$alkanoylamino-$C_1$–$C_4$alkyl, preferably $C_1$–$C_4$alkanoylamino-$C_1$–$C_4$alkyl, such as formylamino-$C_1$–$C_4$alkyl, acetylamino-$C_1$–$C_4$alkyl, propionylamino-$C_1$–$C_4$alkyl or butyrylamino-$C_1$–$C_4$alkyl, $C_2$–$C_4$alkyl being, for example, ethyl, propyl, isopropyl or butyl.

Lower alkoxycarbonylamino-lower alkoxy is, for example, $C_1$–$C_7$alkoxycarbonylamino-$C_2$–$C_4$alkoxy, preferably $C_1$–$C_4$alkoxycarbonylamino-$C_2$–$C_4$alkoxy, such as methoxycarbonylamino-$C_2$–$C_4$alkoxy, ethoxycarbonylamino-$C_2$–$C_4$alkoxy, propoxycarbonylamino-$C_2$–$C_4$alkoxy or butoxycarbonylamino-$C_2$–$C_4$alkoxy, $C_2$–$C_4$alkoxy being, for example, ethoxy, propoxy, isopropoxy or butoxy.

Lower alkoxycarbonylamino-lower alkyl is, for example, $C_1$–$C_7$alkoxycarbonylamino-$C_2$–$C_4$alkyl, preferably $C_1$–$C_4$alkoxycarbonylamino-$C_2$–$C_4$alkyl, such as methoxycarbonylamino-$C_2$–$C_4$alkyl, ethoxycarbonylamino-$C_2$–$C_4$alkyl, propoxycarbonylamino-$C_2$–$C_4$alkyl or butoxycarbonylamino-$C_2$–$C_4$alkyl, $C_2$–$C_4$alkyl being, for example, ethyl, propyl, isopropyl or butyl.

Lower alkoxy-lower alkoxy carries the terminal lower alkoxy group preferably in a higher position than the α-position and is, for example, $C_1$–$C_7$alkoxy-$C_2$–$C_4$alkoxy, preferably $C_1$–$C_4$alkoxy-$C_2$–$C_4$alkoxy, such as 2-methoxyethoxy, 2-ethoxyethoxy, 3-methoxypropoxy, 3-ethoxypropoxy, 4-methoxybutoxy or 4-ethoxybutoxy.

Piperazino-lower alkoxy is, for example, piperazino-$C_1$–$C_7$alkoxy, preferably piperazino-$C_1$–$C_4$alkoxy, such as piperazinomethoxy, 2-piperazinoethoxy, 3-piperazinopropoxy or 4-piperazinobutoxy.

Piperazino-lower alkyl is, for example, piperazino-$C_1$–$C_7$alkyl, preferably piperazino-$C_1$–$C_4$alkyl, such as piperazinomethyl, 2-piperazinoethyl, 3-piperazinopropyl or 4-piperazinobutyl.

Piperidino-lower alkoxy is, for example, piperidino-$C_1$–$C_7$alkoxy, preferably piperidino-$C_1$–$C_4$alkoxy, such as piperidinomethoxy, 2-piperidinoethoxy, 3-piperidinopropoxy or 4-piperidinobutoxy.

Piperidino-lower alkyl is, for example, piperidino-$C_1$–$C_7$alkyl, preferably piperidino-$C_1$–$C_4$alkyl, such as piperidinomethyl, 2-piperidinoethyl, 3-piperidinopropyl or 4-piperidinobutyl.

Pyrrolidino-lower alkoxy is, for example, pyrrolidino-$C_1$–$C_7$alkoxy, preferably pyrrolidino-$C_1$–$C_4$alkoxy, such as pyrrolidinomethoxy, 2-pyrrolidinoethoxy, 3-pyrrolidinopropoxy or 4-pyrrolidinobutoxy.

Pyrrolidino-lower alkyl is, for example, pyrrolidino-$C_1$–$C_7$alkyl, preferably pyrrolidino-$C_1$–$C_4$alkyl, such as pyrrolidinomethyl, 2-pyrrolidinoethyl, 3-pyrrolidinopropyl or 4-pyrrolidinobutyl.

Thiomorpholino-lower alkoxy is, for example, thiomorpholino-$C_1$–$C_7$alkoxy, preferably thiomorpholino-$C_1$–$C_4$alkoxy, such as thiomorpholinomethoxy, 2-thiomorpholinoethoxy, 3-thiomorpholinopropoxy or 4-thiomorpholinobutoxy.

Thiomorpholino-lower alkyl is, for example, thiomorpholino-$C_1$–$C_7$alkyl, preferably thiomorpholino-$C_1$–$C_4$alkyl, such as thiomorpholinomethyl, 2-thiomorpholinoethyl, 3-thiomorpholinopropyl or 4-thiomorpholinobutyl.

Lower alkylene or aza-, oxa- or thia-lower alkylene is, for example, 4- to 6-membered pyrrolidino, piperidino, morpholino or free or S-oxidized thiomorpholino.

Lower alkylamino is, for example, $C_1$–$C_7$alkylamino, such as methyl-, ethyl-, propyl- or butylamino, but can also be isobutylamino, secondary butylamino, tertiary butylamino or a $C_5$–$C_7$alkylamino group, such as a pentylamino, hexylamino or heptylamino group.

Since the compounds according to the invention have at least two optically active carbon atoms, they can therefore be present in the form of stereoisomers, stereoisomer mixtures and in the form of the (essentially) pure diastereomers. Corresponding stereoisomers are likewise encompassed by the present invention.

Preferred compounds of the formula I are those in which the C atom to which the group —$X_1$—$R_2$ is bonded (essentially) has the R configuration and the C atom to which the group —$N(R_3)(R_4)$ is bonded (essentially) has the S configuration according to Cahn-Ingold-Prelog.

The compounds of the formula I have basic or, if $R_3$ and/or $R_4$ is carboxyl or substituted by carboxyl, amphoteric character and can therefore form acid addition salts and, if desired, internal salts.

Acid addition salts of compounds of the formula I are, for example, pharmaceutically acceptable salts thereof with suitable mineral acids, such as halohydric acids, sulfuric acid or phosphoric acid, e.g. hydrochlorides, hydrobromides, sulfates, hydrogensulfates or phosphates, or salts with suitable aliphatic or aromatic sulfonic acids or N-substituted sulfamic acids, e.g. methanesulfonates, benzenesulfonates, p-toluenesulfonates or N-cyclohexylsulfamates (cyclamates).

Pharmaceutically unsuitable salts can also be used for isolation or purification. Only the pharmaceutically acceptable, non-toxic salts are suitable for therapeutic use, and are therefore preferred.

The compounds prepared according to the invention including the compound (2R*,4S*)-N-[1-(3,5-bistrifluoromethylbenzoyl)-2-(4-nitrobenzyl)piperidin-4-yl]acetamide have useful pharmacological properties. In particular, they show a pronounced antagonistic action against substance P and have the typical property spectrum for substance P antagonists. The binding of $^3$H-substance P to the bovine retina in the radioreceptor assay according to H. Bittiger, Ciba Foundation Symposium 91, 196–199 (1982) is thus inhibited in vitro at concentrations from approximately 0.01 μmol/l by the compounds of the formula I and their pharmaceutically acceptable salts. The following in vitro values were thus determined, for example, for the target compounds of Examples 2, 16 (2nd compound), 28 and 45 (c) and (f): 10 nM–11 nM–11 nM–7.6 nM–9 nM.

Substance P is a naturally occurring undecapeptide of the tachykinin family. It is produced and deposited in sensory neurones of the spinal chord and of the brain of mammals and acts pharmacologically as a neurotransmitter and/or neuromodulator. The substance P antagonists of the formula I prepared according to the invention and their pharmaceutically acceptable salts are metabolically stable and are therefore eminently suitable for the prophylactic and therapeutic treatment of disorders in which substance P plays an important part, for example in attacks of pain, in migraine, in disorders of the central nervous system, such as anxiety states, schizophrenia and depression, in certain motor disorders, such as Parkinson's disease, in inflammatory disorders, such as rheumatoid arthritis and osteoarthritis, in disorders of the respiratory organs, such as asthma, chronic bronchitis and chronic rhinitis, in disorders of the gastrointestinal system, such as ulcerative colitis and Crohn's disease, in emesis, in particular chemically induced emesis, and in hypertension. Furthermore, the compounds according to the invention may be used for the inhibition of angiogenesis and may protect against sun burn.

The substance P antagonists of the formula I prepared according to the invention and their pharmaceutically acceptable salts, including the compound (2R*,4S*)-N-[1-(3,5-bis-trifluoromethylbenzoyl)-2-(4-nitrobenzyl)piperidin-4-yl]acetamide, accordingly are eminently suitable for the therapeutic treatment of the disorders mentioned. The industrial production of the active substances is also included in the production of the medicaments.

The invention relates primarily to compounds of the formula I, in which $R_1$ is a benzoyl, naphthoyl or cycloalkanoyl radical which is unsubstituted or substituted by lower alkyl, lower alkoxy, halogen and/or trifluoromethyl, $R_2$ is 3- to 8-membered cycloalkyl or a phenyl or naphthyl radical which is unsubstituted or substituted by lower alkyl, lower alkoxy, halogen, nitro, cyano and/or trifluoromethyl $R_3$ is lower alkyl, di-lower alkylamino, lower alkoxy-lower alkyl or a radical of the formula —$(CH_2)_n$—$C(=O)$—$R_5$ (Ia) and $R_4$ is hydrogen, lower alkyl or a radical of the formula —$(CH_2)_n$—$C(=O)$—$R_5$ (Ia) or $R_3$ and $R_4$ together are 4- to 6-membered lower alkylene or aza-, oxa- or thia-lower alkylene, $R_5$ is hydrogen, lower alkyl, halo-lower alkyl, amino-lower alkyl, N-mono- or N,N-di-lower alkylamino-lower alkyl, lower alkanoylamino-lower alkyl, lower alkoxycarbonylamino-lower alkyl, pyrrolidino-lower alkyl, piperidino-lower alkyl, free or N'-lower alkylated or N'-lower alkanoylated piperazino-lower alkyl, morpholino-lower alkyl, free or S-oxidized thiomorpholino-lower alkyl, lower alkanoylamino-lower alkyl, lower alkoxycarbonylamino-lower alkyl or 4- to 6-membered lower alkylenamino- or aza-, oxa- or thia-lower alkylenamino-lower alkyl, lower alkoxy, lower alkoxy-lower alkoxy, amino-lower alkoxy, N-mono- or N,N-di-lower alkylamino-lower alkoxy, lower alkanoylamino-lower alkoxy, lower alkoxycarbonyl amino-lower alkoxy, pyrrolidino-lower alkoxy, piperidino-lower alkoxy, free or N'-lower alkylated or N'-lower alkanoylated piperazino-lower alkoxy, morpholino-lower alkoxy or free or S-oxidized thiomorpholino-lower alkoxy, $X_1$ is methylene, ethylene, a direct bond, a free or ketalized carbonyl group, or hydroxymethylene and n is 0 or 1, and their salts.

The invention relates in particular to compounds of the formula I, in which $R_1$ is a benzoyl, naphthoyl or cycloalkanoyl radical which is unsubstituted or substituted by $C_1$–$C_4$alkyl, such as methyl, $C_1$–$C_4$alkoxy, such as methoxy, halogen, such as chlorine, and/or trifluoromethyl, $R_2$ is 3- to 8-membered cycloalkyl or a phenyl or naphthyl radical which is unsubstituted or substituted by $C_1$–$C_4$alkyl, such as methyl, $C_1$–$C_4$alkoxy, such as methoxy, halogen, nitro, cyano and/or trifluoromethyl, $R_3$ is $C_1$–$C_7$alkyl, such as isopropyl, secondary butyl, isobutyl or neopentyl, di-$C_1$–$C_4$alkylamino-$C_1$–$C_4$alkyl, such as dimethylaminomethyl, 2-dimethylaminoethyl, 3-dimethylaminopropyl, 4-dimethylaminobutyl, 3-diethylaminopropyl or 3-(N-ethyl-N-methylamino)propyl, $C_1$–$C_4$alkoxy-$C_1$–$C_4$alkyl, such as 2-methoxyethyl, 2-ethoxyethyl or 3-methoxypropyl, or a radical of the formula —($CH_2$)$_n$—C(=O)—$R_5$ (Ia) and $R_4$ is hydrogen, $C_1$–$C_4$alkyl, such as methyl, or a radical of the formula —($CH_2$)$_n$—C(=O)—$R_5$ (Ia) or $R_3$ and $R_4$ together are $C_4$–$C_6$alkylene or 3-aza-, 3-oxa- or 3-thia-$C_4$–$C_6$alkylene and, together with the N atom bonding them, are preferably pyrrolidino, piperidino, morpholino or free or S-oxidized thiomorpholino, $R_5$ is hydrogen, $C_1$–$C_7$alkyl, such as methyl, ethyl, propyl, isopropyl, butyl, secondary butyl, isobutyl or neopentyl, trihalo-$C_1$–$C_4$alkyl, such as trifluoromethyl, trifluoroethyl or trifluoropropyl, amino-$C_1$–$C_4$alkyl, such as aminomethyl, 2-aminoethyl, 3-aminopropyl or 4-aminobutyl, N-$C_1$–$C_4$alkylamino-$C_1$–$C_4$alkyl, such as methylaminomethyl, 2-methylaminoethyl, ethylaminomethyl, 2-ethylaminoethyl, propylaminomethyl, 2-propylaminoethyl, dibutylaminomethyl, di-$C_1$–$C_4$alkylamino-$C_1$–$C_4$alkyl, such as dimethylaminomethyl, 2-dimethylaminoethyl, 3-dimethylaminopropyl, 4-dimethylaminobutyl, 3-diethylaminopropyl or 3-(N-ethyl-N-methylamino) propyl, $C_1$–$C_7$alkanoylamino-$C_1$–$C_4$alkyl, such as formylaminomethyl, 2-formylaminoethyl, acetylaminomethyl, 2-acetylaminoethyl, propionylaminomethyl, 2-propionylaminoethyl or butyrylaminomethyl, $C_1$–$C_4$alkoxycarbonylamino-$C_1$–$C_4$alkyl, such as methoxycarbonylaminomethyl, ethoxycarbonylaminomethyl, isopropoxycarbonylaminomethyl, 2-methoxycarbonylaminoethyl, 2-ethoxycarbonylaminoethyl, 2-isopropoxycarbonylaminoethyl or tertiary butoxycarbonylaminomethyl, pyrrolidino-$C_1$–$C_4$alkyl, piperidino-$C_1$–$C_4$alkyl, free or N'-$C_1$–$C_4$alkylated, such as N'-$C_1$–$C_4$methylated, or N'-$C_1$–$C_4$-alkanoylated, such as N'-$C_1$–$C_4$-acetylated, piperazino-$C_1$–$C_4$alkyl, morpholino-$C_1$–$C_4$alkyl, free or S-oxidized thiomorpholino-$C_1$–$C_4$alkyl, such as pyrrolidinomethyl, piperidinomethyl, N'-$C_1$–$C_4$alkylated, such as N'-$C_1$–$C_4$-methylated, or N'-$C_1$–$C_4$alkanoylated, such as N'-$C_1$–$C_4$-acetylated, piperazinomethyl, morpholinomethyl, free or S-oxidized thiomorpholinomethyl, $C_1$–$C_4$alkanoylamino-$C_1$–$C_4$alkyl, such as formylaminomethyl, acetylaminomethyl, propionylaminomethyl or butyrylaminomethyl, $C_1$–$C_4$alkoxycarbonylamino-$C_2$–$C_4$alkyl, such as methoxycarbonylaminoethyl, ethoxycarbonylaminoethyl, propoxycarbonylaminoethyl or butoxycarbonylaminoethyl, $C_1$–$C_7$alkoxy, such as methoxy, ethoxy, propoxy, isopropoxy or butoxy, 5- to 7-membered cycloalkoxy, such as cyclohexyloxy, $C_1$–$C_4$alkoxy-$C_2$–$C_4$alkoxy, such as 2-methoxyethoxy, 2-ethoxyethoxy, 3-methoxypropoxy, 3-ethoxypropoxy, 4-methoxybutoxy or 4-ethoxybutoxy, amino-$C_1$–$C_7$alkoxy, preferably amino-$C_2$–$C_4$alkoxy, such as 2-aminoethoxy, 3-aminopropoxy or 4-aminobutoxy, N-mono- or N,N-di-$C_1$–$C_4$alkylamino-$C_1$–$C_4$alkoxy, such as methylamino or dimethylaminomethoxy, 2-methylamino- or 2-dimethylaminoethoxy, 3-methylamino- or 3-dimethylaminopropoxy, ethylamino- or diethylaminomethoxy, 2-ethylamino- or 2-diethylaminoethoxy, N-ethyl-N-methylaminomethoxy, propylaminomethoxy, diisopropylaminomethoxy or butylaminomethoxy, pyrrolidino-$C_1$–$C_4$alkoxy, such as pyrrolidinomethoxy, piperidino-$C_1$–$C_4$alkoxy, such as piperidinomethoxy, morpholino-$C_1$–$C_4$alkoxy, such as morpholinomethoxy, or free or S-oxidized thiomorpholino-$C_1$–$C_4$alkoxy, such as thiomorpholinomethoxy, and $X_1$ is methylene, ethylene, a direct bond, a free or ketalized carbonyl group, hydroxymethylene or $C_1$–$C_4$alkoxymethylene, such as methoxymethylene, ethoxymethylene, propoxymethylene or butoxymethylene, and n is 0 or 1, and their salts.

The invention relates in particular to compounds of the formula I in which $R_1$ is benzoyl which is unsubstituted or substituted by lower alkyl, lower alkoxy, halogen and/or trifluoromethyl, $R_2$ is phenyl which is unsubstituted or substituted by lower alkyl, lower alkoxy, halogen, nitro, cyano and/or trifluoromethyl or unsubstituted naphthyl, $R_3$ is lower alkyl which is unsubstituted or substituted by carboxyl, lower alkoxycarbonyl, lower alkoxy-lower alkoxycarbonyl, 5- to 7-membered cycloalkoxycarbonyl, carbamoyl, N-mono- or N,N-di-lower alkylcarbamoyl or lower alkylamino, lower alkanoyl which is unsubstituted or substituted by halogen, amino, N-mono- or N,N-di-lower alkylamino, lower alkanoylamino or morpholino, or lower alkoxycarbonyl or lower alkylamino-lower alkoxycarbonyl and $R_4$ is hydrogen or lower alkyl which is unsubstituted or substituted by carboxyl, lower alkoxycarbonyl, lower alkoxy-lower alkoxycarbonyl, 5- to 7-membered cycloalkoxycarbonyl, carbamoyl, N-mono- or N,N-di-lower alkylcarbamoyl or lower alkylamino or $R_3$ and $R_4$, together with the N atom bonding them, are pyrrolidino, piperidino, morpholino or thiomorpholino and $X_1$ is methylene, and their salts.

The invention relates first of all to compounds of the formula I in which $R_1$ is a benzoyl, naphthoyl or cycloalkanoyl radical which is unsubstituted or substituted by $C_1$–$C_4$alkyl, such as methyl, $C_1$–$C_4$alkoxy, such as methoxy, halogen, such as chlorine, and/or trifluoromethyl, $R_2$ is phenyl which is unsubstituted or substituted by $C_1$–$C_4$alkyl, such as methyl, $C_1$–$C_4$alkoxy, such as methoxy, or halogen, nitro, cyano and/or trifluoromethyl, or unsubstituted naphthyl, $R_3$ is $C_3$–$C_7$alkyl, such as isobutyl or neopentyl, $C_1$–$C_4$alkoxycarbonyl-$C_1$–$C_4$alkyl, such as methoxycarbonylmethyl, isopropoxycarbonylmethyl or tertiary butoxycarbonylmethyl, $C_1$–$C_4$alkoxy-$C_2$–$C_4$alkoxycarbonyl-$C_1$–$C_4$alkyl, such as 2-ethoxyethoxycarbonylmethyl or 2-methoxyethoxycarbonylmethyl, 5- to 7-membered cycloalkoxycarbonyl-$C_1$–$C_4$alkyl, such as cyclohexyloxycarbonylmethyl, carbamoyl-$C_1$–$C_4$alkyl, such as carbamoylmethyl, N-$C_1$–$C_4$alkylcarbamoyl-$C_1$–$C_4$alkyl, such as isopropylcarbamoylmethyl, N,N-di-$C_1$–$C_4$alkylcarbamoyl-$C_1$–$C_4$alkyl, such as 2-dimethylaminocarbamoylmethyl, N-$C_1$–$C_4$alkylamino-$C_1$–$C_4$alkyl, such as 3-dimethylaminopropyl, $C_1$–$C_7$alkanoyl, such as formyl, acetyl, propionyl or butyryl, trihalo-$C_1$–$C_7$alkanoyl, such as trifluoroacetyl, amino-$C_1$–$C_7$alkanoyl, such as glycinyl, N-$C_1$–$C_4$alkylamino-$C_1$–$C_4$alkanoyl, such as tertiary butylaminoacetyl, N,N-di-$C_1$–$C_4$alkylamino-$C_1$–$C_4$alkanoyl, such as dimethylaminoacetyl, morpholino-$C_1$–$C_7$alkanoyl, such as morpholinoacetyl, $C_1$–$C_7$alkanoylamino-$C_1$–$C_4$alkanoyl, such as acetylaminoacetyl, $C_1$–$C_4$alkoxycarbonyl, such as isobutoxycarbonyl, or N,N-di-$C_1$–$C_4$alkylamino-$C_2$–$C_4$alkoxycarbonyl, such as 2-dimethylaminoethoxycarbonyl, and $R_4$ is hydrogen or $C_1$–$C_4$alkoxycarbonyl-$C_1$–$C_4$alkyl, such as methoxycarbonylmethyl, isopropoxycarbonylmethyl or tertiary butoxycarbonylmethyl, $C_1$–$C_4$alkoxy-$C_2$–$C_4$alkoxycarbonyl-$C_1$–$C_4$alkyl, such as 2-ethoxyethoxycarbonylmethyl or 2-methoxyethoxycarbonylmethyl, 5- to 7-membered cycloalkoxycarbonyl-$C_1$–$C_4$alkyl, such as cyclohexyloxycarbonylmethyl, carbamoyl-$C_1$–$C_4$alkyl, such as carbamoylmethyl, N-$C_1$–$C_4$alkylcarbamoyl-$C_1$–$C_4$alkyl, such as isopropylcarbamoylmethyl, N,N-di-$C_1$–$C_4$alkylcarbamoyl-$C_1$–$C_4$alkyl, such as 2-dimethylaminocarbamoylmethyl, N-$C_1$–$C_4$alkylamino-$C_1$–$C_4$alkyl, such as 3-dimethylaminopropyl, or $R_3$ and $R_4$, together with the N atom bonding them, are morpholino and $X_1$ is methylene, and their salts.

The invention relates primarily to a compound of the formula I in which $R_1$ is a benzoyl, naphthoyl or 3- to 8-membered cycloalkanoyl radical which is unsubstituted or substituted by lower alkyl, lower alkoxy, halogen and/or trifluoromethyl;

$R_2$ is 3- to 8-membered cycloalkyl or a phenyl or naphthyl radical which is unsubstituted or substituted by lower alkyl, lower alkoxy, halogen, nitro, cyano and/or trifluoromethyl;

$R_3$ and $R_4$ together are lower alkylene or aza-, oxa- or thia-lower alkylene;

or $R_3$ is lower alkyl, lower alkoxy-lower alkyl, di-lower alkylamino-lower alkyl or a radical of the formula —$(CH_2)_n$—C(=O)—$R_5$ (Ia); and $R_4$ is hydrogen, lower alkyl or a radical of the formula —$(CH_2)_n$—C(=O)—$R_6$ (Ia);

$R_5$ is (i) hydrogen, $C_1$–$C_4$alkyl or $C_1$–$C_4$alkyl which is substituted by halogen, lower alkoxy, amino or amino which is substituted by lower alkyl, amino-lower alkyl, mono- or di-lower alkylaminoalkyl, lower alkanoyl, lower alkoxycarbonyl or lower alkylene or 3-aza-, 3-oxa- or 3-thia-$C_4$–$C_6$alkylene, (ii) hydroxyl, 3- to 8-membered cycloalkoxy, lower alkoxy or lower alkoxy which is substituted by lower alkoxy, amino or amino which is substituted by lower alkyl, amino-lower alkyl, mono- or di-lower alkylaminoalkyl, lower alkanoyl, lower alkoxycarbonyl or lower alkylene or 3-aza-, 3-oxa- or 3-thia-$C_4$–$C_6$alkylene, or (iii) amino or amino which is substituted by lower alkyl, 3- to 8-membered cycloalkyl, amino-lower alkyl, mono- or di-lower alkylaminoalkyl, lower alkanoyl, lower alkoxycarbonyl or lower alkylene or 3-aza-, 3-oxa- or 3-thia-$C_4$–$C_6$alkylene;

$X_1$ is methylene, ethylene, a direct bond, a carbonyl group, di-lower alkoxymethylene, hydroxymethylene or lower alkoxymethylene; and n is 0 or 1;

or a salt thereof.

The invention relates primarily to a compound of the formula I in which $R_1$ is a benzoyl or naphthoyl radical which is unsubstituted or substituted by lower alkyl, lower alkoxy, halogen and/or trifluoromethyl;

$R_2$ is 5- to 7-membered cycloalkyl or a phenyl or naphthyl radical which is unsubstituted or substituted by lower alkyl, lower alkoxy, halogen, nitro, cyano and/or trifluoromethyl;

$R_3$ and $R_4$ together are $C_4$–$C_6$alkylene or 3-aza-, 3-oxa- or 3-thia-$C_4$–$C_6$alkylene, in 3-aza-, 3-oxa- or 3-thiapentylene, or $R_3$ is lower alkyl, lower alkoxy-lower alkyl, di-lower alkylamino-lower alkyl or a radical of the formula —$(CH_2)_n$—C(=O)—$R_5$ (Ia); and $R_4$ is hydrogen, lower alkyl or a radical of the formula —$(CH_2)_n$—C(=O)—$R_5$ (Ia);

$R_5$ is (i) hydrogen, $C_1$–$C_{14}$alkyl or $C_1$–$C_{14}$alkyl, which is substituted by halogen, lower alkoxy, amino or amino which is substituted by lower alkyl, amino-lower alkyl, mono- or di-lower alkylaminoalkyl, lower alkanoyl, lower alkoxycarbonyl or $C_4$–$C_6$alkylene or 3-aza-, 3-oxa- or 3-thia-$C_4$–$C_6$alkylene, in particular 3-aza-, 3-oxa- or 3-thiapentylene, (ii) hydroxyl, 3- to 8-membered cycloalkoxy, lower alkoxy or lower alkoxy which is substituted by lower alkoxy, amino or amino which is substituted by lower alkyl, amino-lower alkyl, mono- or di-lower alkylaminoalkyl, lower alkanoyl, lower alkoxycarbonyl or $C_4$–$C_6$alkylene or 3-aza-, 3-oxa- or 3-thia-$C_4$–$C_6$alkylene, in particular 3-aza-, 3-oxa- or 3-thiapentylene, or (iii) amino or amino which is substituted by lower alkyl, $C_5$–$C_7$cycloalkyl, amino-lower alkyl, mono- or di-lower alkylaminoalkyl, lower alkanoyl, lower alkoxycarbonyl or $C_4$–$C_6$alkylene or 3-aza-, 3-oxa- or 3-thia-$C_4$–$C_6$alkylene, in particular 3-aza-, 3-oxa- or 3-thiapentylene;

$X_1$ is methylene, ethylene, a direct bond, a carbonyl group, di-lower alkoxymethylene, hydroxymethylene or lower alkoxymethylene; and n is 0 or 1;

or a salt thereof.

The invention relates primarily to a compound of the formula I in which $R_1$ is benzoyl or benzoyl which is substituted by lower alkyl, lower alkoxy, halogen and/or trifluoromethyl;

$R_2$ is phenyl, phenyl which is substituted by lower alkyl, lower alkoxy, halogen, nitro, cyano and/or trifluoromethyl, or naphthyl;

$R_3$ and $R_4$ together are $C_4$–$C_6$alkylene; or $R_3$ is lower alkyl, di-lower alkylamino-lower alkyl or a radical of the formula —$(CH_2)_n$—C(=O)—$R_5$ (Ia);

and $R_4$ is hydrogen, lower alkyl or a radical of the formula —$(CH_2)_n$—C(=O)—$R_5$ (Ia);

$R_5$ is (i) hydrogen, lower alkyl or halo-lower alkyl; (ii) hydroxyl, $C_4$–$C_6$cycloalkoxy, lower alkoxy, lower alkoxy-lower alkoxy or di-lower alkylamino-lower alkoxy; or (iii) amino, lower alkylamino, di-lower alkylamino, $C_5$–$C_7$cycloalkyl-amino or di-lower alkylamino-lower alkylamino;

$X_1$ is methylene; and n is 0 or 1;

or a salt thereof.

The invention relates first of all to a compound of the formula I in which $R_1$ is benzoyl or benzoyl which is substituted by lower alkyl, lower alkoxy, halogen and/or trifluoromethyl;

$R_2$ is phenyl, phenyl which is substituted by lower alkyl, lower alkoxy, halogen, nitro, cyano and/or trifluoromethyl, or naphthyl;

$R_3$ and $R_4$ together are $C_4$–$C_6$alkylene; or $R_3$ is lower alkyl, di-lower alkylamino-lower alkyl or a radical of the formula —$(CH_2)_n$—C(=O)—$R_5$ (Ia); and $R_4$ is hydrogen;

$R_5$ is (i) hydrogen, lower alkyl or halo-lower alkyl; (ii) hydroxyl, $C_4$–$C_6$cycloalkoxy, lower alkoxy, lower alkoxy-lower alkoxy or di-lower alkylamino-lower alkoxy, or (iii) amino, lower alkylamino, di-lower alkylamino, $C_5$–$C_7$cycloalkylamino or di-lower alkylamino-lower alkylamino;

$X_1$ is methylene; and n is 0 or 1;

or a salt thereof.

The invention relates first of all to a compound of the formula I in which $R_1$ is benzoyl which is disubstituted by $C_1$–$C_4$alkyl, $C_1$–$C_4$alkoxy, halogen and/or trifluoromethyl, in particular in positions 3 and 5;

$R_2$ is phenyl, phenyl which is substituted by $C_1$–$C_4$alkyl, $C_1$–$C_4$alkoxy, halogen, nitro, cyano and/or trifluoromethyl, in particular in position 4, or naphthyl;

(i) $R_3$ is a radical of the formula —$(CH_2)_n$—C(=O)—$R_5$ (Ia); $R_4$ is hydrogen; n is 0 and $R_5$ is $C_1$–$C_7$alkyl, $C_5$–$C_7$cycloalkylamino or di-$C_1$–$C_4$alkylamino-$C_2$–$C_4$alkoxy; or (ii) $R_3$ is a radical of the formula —$(CH_2)_n$—C(=O)—$R_5$ (Ia); $R_4$ is hydrogen; n is 1; and $R_5$ is amino; and $X_1$ is methylene;

or a salt thereof.

The invention relates first of all to a compound of the formula I in which $R_1$ is benzoyl which is disubstituted by trifluoromethyl, in particular in positions 3 and 5;

$R_2$ is phenyl or phenyl which is monosubstituted by halogen, such as chlorine, in particular in position 4;

$R_3$ is a radical of the formula —$(CH_2)_n$—C(=O)—$R_5$ (Ia);

$R_4$ is hydrogen;

$R_5$ is $C_1$–$C_7$alkyl, such as ethyl or propyl, $C_5$–$C_7$cycloalkylamino, such as cyclohexylamino, or di-$C_1$–$C_4$alkylamino-$C_2$–$C_4$alkoxy, such as 3-dimethylaminopropoxy;

n is 0; and $X_1$ is methylene;

or a salt thereof.

The invention relates first of all to a compound of the formula I in which $R_1$ is 3,5-bistrifluoromethylbenzoyl;

$R_2$ is phenyl or phenyl which is monosubstituted by halogen, such as chlorine, in particular in position 4;

$R_3$ is a radical of the formula —$(CH_2)_n$—C(=O)—$R_5$ (Ia);

$R_4$ is hydrogen; n is 0;

$R_5$ is $C_1$–$C_4$alkyl, such as ethyl or propyl, or $C_5$–$C_7$cycloalkylamino, such as cyclohexylamino; and $X_1$ is methylene;

or a salt thereof.

The invention relates especially to the compounds of the formula I mentioned in the examples and to their salts, in particular their pharmaceutically acceptable salts.

The invention also relates to a process for the preparation of the compounds according to the invention based on methods known per se. This is characterized in that a) the radical $R_1$ is introduced into a compound of the formula II

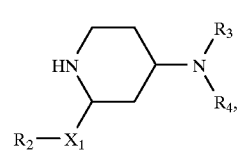

in which $R_2$, $R_3$, $R_4$ and $X_1$ are as defined, or b) compounds of the formulae III

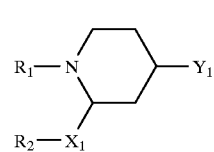

and $Y_2$-$R_3$ (IV), in which $Y_1$ is a group of the formula —N($R_4$)—H and $Y_2$ is hydroxyl, reactive esterified hydroxyl or, if $R_3$ is a radical of the formula —$(CH_2)_n$—C(=O)—$R_5$ (Ia) and n is 0, is etherified hydroxyl or $Y_1$ is free or reactive esterified hydroxyl and $Y_2$ is a group of the formula -N($R_4$)-H, $R_1$, $R_2$, $R_3$, $R_4$ and $X_1$ being as defined, or their salts are condensed with one another or c) for the preparation of compounds of the formula I, in which $R_4$ is hydrogen, the group $Y_3$ is removed from a compound of the formula V

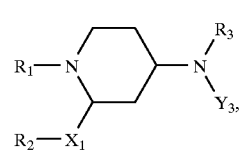

in which $Y_3$ is an amino protective group and $R_1$, $R_2$, $R_3$ and $X_1$ are as defined, or from a salt thereof or d) for the preparation of compounds of the formula I, in which $R_3$ is lower alkyl, di-lower alkylamino-lower alkyl or lower alkoxy-lower alkyl and $R_4$ is hydrogen or lower alkyl, a compound of the formula VI

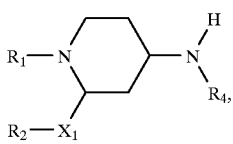

in which $R_1$, $R_2$, $R_4$ and $X_1$ are as defined, or a salt thereof is reacted under reducing conditions with an appropriate aldehyde of the formula O=CH—R (VII) or e) for the preparation of compounds of the formula I, in which $R_3$ and $R_4$ together are lower alkylene or aza-, oxa- or thia-lower alkylene, a compound of the formula VIII

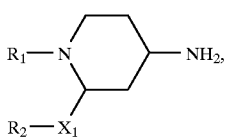

in which $R_1$, $R_2$ and $X_1$ are as defined, or a salt thereof is condensed with a reactive diester of an appropriate lower alkanediol or aza-, oxa- or thia-lower alkanediol or f) for the preparation of compounds of the formula I, in which $X_1$ is a carbonyl or hydroxymethylene group, compounds of the formulae IX

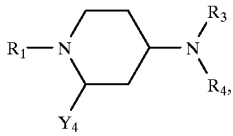

and $Y_5$–$R_2$ (X), in which one of the radicals $Y_4$ and $Y_5$ is formyl or a carboxyl group which is free, converted into an anhydride or esterified, and the other is a metallic radical and $R_2$, $R_3$ and $R_4$ are as defined, are condensed with one another and, if desired, a compound which is obtained is converted into another compound of the formula I, an isomer mixture obtainable according to the process is separated into the components and the preferred isomer is in each case separated off and/or a free compound obtainable according to the process is converted into a salt or a salt obtainable according to the process is converted into the corresponding free compound.

The reactions according to the process and the preparation of novel starting substances or intermediates are carried out in analogy to the manner of reaction and formation of known starting substances or intermediates. Even if not expressly mentioned below, the auxiliaries customary in each case, such as catalysts, condensing and solvolysis agents and/or solvents or diluents, and reaction conditions, such as temperature and pressure conditions, and also, if desired, protective gases are used here.

Salts of starting materials which have at least one basic centre, for example of the formulae II or VI, are corresponding acid addition salts, while salts of starting substances which have an acidic group are present as salts with bases, in each case as mentioned above in connection with corresponding salts of the formula I.

The reactions described hereinbefore and hereinafter in the variants are carried out in a manner known per se, e.g. in the absence or, customarily, in the presence of a suitable solvent or diluent or of a mixture thereof, the reaction being carried out, if required, with cooling, at room temperature or with heating, e.g. in a temperature range from approximately −80° C. up to the boiling point of the reaction medium, preferably from approximately −10° to approximately +200° C., and, if necessary, in a closed vessel, under pressure, in an inert gas atmosphere and/or under anhydrous conditions.

The introduction of the radical $R_1$ by reaction with an agent introducing the radical $R_1$ according to process variant a) is carried out in a customary manner, for example by reaction with an N-acylating agent of the formula $R_1$-$Y_a$ (IIA), in which $R_1$ has one of the definitions given at the beginning and $Y_a$ is free or etherified hydroxyl, such as hydroxyl, lower alkoxy or unsubstituted or substituted phenoxy, or reactive esterified hydroxyl, such as halogen, in particular chlorine, or a radical of the formula —O—$R_1$.

If necessary, the reaction is carried out with thermal decomposition of intermediately formed ammonium salts or in the presence of a condensing agent, such as a dehydrating agent, or basic condensing agents, and in the presence of a solvent or diluent. Customary condensing agents are, for example, carbodiimides, such as diethyl-, dipropyl-, N-ethyl-N'-(3-dimethylaminopropyl)carbodiimide or, in particular, dicyclohexylcarbodiimide, and also suitable carbonyl compounds, for example carbonyldiimidazole, 1,2-oxazolium compounds, e.g. 2-ethyl-5-phenyl-1,2-oxazolium-3'-sulphonate and 2-tert-butyl-5-methylisoxazolium perchlorate, or a suitable acylamino compound, e.g. 2-ethoxy-1-ethoxycarbonyl-1,2-dihydroquinoline, and also activated phophoric acid derivatives, e.g. diphenylphosphoryl azide, diethylphosphoryl cyanide, phenyl N-phenylphosphoramidochloridate, bis (2-oxc-3-oxazolidinyl)phosphinoyl chloride or 1-benzotriazolyloxytris(dimethylamino)phosphonium hexafluorophosphate. The reaction is thus performed using acids (IIA1; Y=COOH) preferably in the presence of a dehydrating agent, such as of N,N-dicyclohexylcarbodiimide or with thermal decomposition of the ammonium salt primarily formed, while the reaction with acid anhydrides (IIA1; Y=halogen or —O—(C=O)—$R_1$) is preferably carried out in the presence of a basic condensing agent, such as of an alkali metal hydroxide or carbonate, e.g. potassium carbonate, or of a tertiary or sterically hindered secondary organic amine, such as of a tri-lower alkylamine, e.g. of triethylamine or diisopropylamine, or of an aromatic nitrogen base, e.g. of pyridine.

The starting substances of the formula II can be prepared in a customary manner, preferably by introducing the radical $R_3$ and, if desired, $R_4$ into a 2-($R_2$-$X_1$)-aminopiperidine intermediately protected in position 1 by an amino protective group, e.g. by tertiary butoxycarbonyl, and removing the amino protective group in a customary manner, for example by treating with trifluoroacetic acid. If $R_4$ is hydrogen, the corresponding starting compound of the formula II protected by trifluoroacetyl on the exocyclic N atom is obtained in this case. The introduction of the radical $R_3$ and, if desired, $R_4$, is in this case preferably carried out as described hereinafter under process variant b).

Starting substances of the formula II in which $R_3$ is a group of the formula —(CH$_2$)$_n$—(C=O)—$R_5$ (Ia) in which n is 0 and $R_5$ is unsubstituted lower alkyl or lower alkyl which is substituted by halogen, lower alkoxy or unsubstituted amino or amino which is substituted by lower alkyl, lower alkanoyl, lower alkoxycarbonyl or lower alkylene or aza-, oxa- or thia-lower alkylene, and $R_4$ is hydrogen or lower alkyl, can preferably be prepared by treating a lower alkyl N-[1-($X_1$-$R_2$)but-3-enyl]carbamate with sodium hydride, for example in boiling tetrahydrofuran, and then reacting with a chloromethyl lower alkyl ether, reacting the N-lower alkoxymethyl-N-[1-($X_1$-$R_2$)but-3-enyl]carbamate obtained with a corresponding nitrile of the formula $R_5$—CN and chlorosulfonic acid with cooling and removing the esterified 1-carboxylic acid group from the 2-($X_1$-$R_2$)-4-($R_5$CO)-piperidine-1-carboxylic acid ester obtained, e.g. by treatment with hydrogen bromide in acetic acid.

In starting substances of the formula III or IV according to process variant b), reactive esterified hydroxyl is, for example, a halogen atom, such as chlorine, bromine or iodine, or, if $R_3$ has a saturated C atom in the α-position, e.g. if n is 1, a sulphonyloxy group, e.g. methanesulfonyloxy or p-toluenesulfonyloxy, or if $R_3$ has a carbonyl group in the α-position, e.g. n is 1, a group of the formula —O—(C=O)—$R_5$. Etherified hydroxyl is, for example, lower alkoxy, such as methoxy or ethoxy, or substituted or unsubstituted phenoxy.

The compounds of the formulae III and IV are reacted in a customary manner, for example with thermal decomposition of intermediately formed ammonium salts or in the presence of a condensing agent, such as of a dehydrating agent, e.g. of N,N-dicyclohexylcarbodiimide or of bis(2-oxo-3-oxazolidinyl)phosphinoyl chloride, or of a basic condensing agent, preferably of pyridine or of a tri-lower alkylamine, e.g. of triethylamine, or of an alkali metal carbonate or hydrogencarbonate, if necessary in the presence of a solvent or diluent.

The reaction is thus performed using acids of the formula IV ($Y_2$=OH), preferably in the presence of bis(2-oxo-3-oxazolidinyl)phosphinoyl chloride and of a tri-lower alkylamine, for example in a halohydrocarbon, such as dichloromethane, or a cyclic aliphatic ether, such as tetrahydrofuran or dioxane.

The reaction with reactive esters of the formula IV or III ($Y_2$or $Y_1$=reactive esterified hydroxyl) or with acid anhydrides of the formula IV ($Y_2$=hydroxyl which is converted into an anhydride) is carried out, in particular, in the presence of a basic condensing agent, such as a heterocyclic base, e.g. pyridine, 4-dimethylaminopyrdine or preferably N-methyl-morpholine, or of a tri-lower alkylamine, e.g. of triethylamine or diisopropylamine, for example in a halohydrocarbon, such as dichloromethane, or a cyclic aliphatic ether, such as tetrahydrofuran or dioxane, or of an aliphatic nitrile, e.g. in acetonitrile. If a primary amine of the formula III ($Y_1$=NH$_2$) is reacted with a β-branched lower alkyl halide of the formula IV ($Y_2$=halogen; $R_3$=lower alkyl) in the presence of an alkali metal carbonate or hydrogencarbonate, the incorporation of carbon dioxide can occur. In addition to or instead of the target compound of the formula I in which $R_3$ is lower alkyl, the corresponding compound of the formula I which is N-substituted by the group —(C=O)—O—$R_3$ is then obtained.

Starting substances of the formula III in which $Y_1$ is primary amino are obtained, for example, by treating an appropriate 4-amino-2-($X_1$-$R_2$)-piperidine or its trifluoroacetate with trifluoroacetic anhydride, condensing the resulting N-[2-($X_1$-$R_2$)piperidin-4-yl]trifluoroacetamide with an N-acylating agent of the formula $R_1$-$Y_a$ (IIA), in which $R_1$ has one of the definitions given at the beginning and $Y_a$ is free, etherified or reactive esterified hydroxyl, for example as indicated under process variant a), and treating the resulting N-[1-$R_1$-2-($X_1$-$R_2$)piperidin-4-yl] trifluoroacetamide with strong, e.g. approximately 5-normal, sodium hydroxide solution.

Starting substances of the formula III, in which $Y_1$ is hydroxyl are obtained, for example, by reacting an appropriate 1-($R_2$-$X_1$)-1-($R_1$-amino)but-3-ene with a halomethyl-lower alkyl ether in the presence of benzyltrimethylammonium bromide, treating the resulting 1-($R_2$-$X_1$)-1-(N-$R_1$-N-lower alkoxymethylamino)but-3-ene with an excess of formic acid and hydrolysing the resulting 1-$R_1$-2-($X_1$-$R_2$) piperidin-4-yl formate with strong hydrochloric acid to give the corresponding 1-$R_1$-2-($X_1$-$R_2$)piperidin-4-ol of the formula III ($Y_1$=hydroxyl). Compounds of the formula III in which $Y_1$ is reactive esterified hydroxyl can be prepared from these by reaction with an agent introducing a reactive esterified hydroxyl group, such as a sulfonyl halide, e.g. with methanesulfonyl chloride, or a halogenating agent, such as thionyl chloride, preferably in the presence of pyridine.

The amino protective group $Y_3$ according to process variant c) is, for example, a free or halogenated lower alkanoyl group, such as trifluoroacetyl, or an acyl group derived from a hemiester of carbonic acid, such as a lower alkoxycarbonyl or (α-phenyl-lower alkoxycarbonyl group, e.g. tertiary butoxycarbonyl or benzyloxycarbonyl, or a silyl group, such as tri-lower alkylsilyl, e.g. trimethylsilyl. The amino protective group is removed in a customary manner, for example by acid treatment, or starting from compounds V, in which $Y_3$ is halogenated lower alkyl, such as trifluoroacetyl, by reductive elimination, for example by treating with a di-light metal hydride, such as sodium borohydride, preferably in a lower alkanol, such as methanol.

The starting substances of the formula V can be prepared, for example, in analogy to process variant a), starting from appropriate N-$Y_3$-N-[2-($X_1$-$R_2$)piperidin-4-yl]amines.

The reaction of compounds of the formula VI with aldehydes of the formula VII according to process variant d) is carried out, for example, in the presence of water and of a hydrogenation catalyst, such as of a platinum or palladium catalyst or of Raney nickel, or in the presence of a di-light metal hydride, such as sodium borohydride or sodium cyanoborohydride, preferably in a solvent which is inert under the reaction conditions, such as of a lower alkanol, such as methanol or ethanol, or of a di-lower alkyl or lower alkylene ether, such as diethyl ether, dioxane or tertrahydrofuran.

In a reactive diester of a lower alkane diol or aza-, oxa- or thia-lower alkanediol according to process variant e), reactive esterified hydroxyl is, for example, a halogen atom, such as chlorine, bromine or iodine, or a sulphonyloxy group, e.g. methanesulfonyloxy or p-toluenesulfonyloxy. The condensation is preferably carried out in the presence of a basic condensing agent, such as of a metal base, e.g. of an alkali metal carbonate, if necessary with heating, e.g. in the temperature range from approximately 60° to approximately 140° C., if desired at elevated pressure.

In starting substances of the formulae IX and X according to process variant f), carboxyl $Y_4$ or $Y_5$ which is free, converted into an anhydride or esterified is, for example, halocarbonyl or, in the case of $Y_5$ a group of the formula $R_2$—C(=O)—O— and a metallic radical $Y_4$ or $Y_5$ is, for example, an alkali metal atom or a group of the formula -M"/2 or M"-hal, in which M" is a metal atom of group IIb of the Periodic Table of the Elements, such as Mg or Zn.

The condensation of compounds of the formulae IX and X is carried out in a customary manner, for example in an ethereal solvent, such as an aliphatic or cycloaliphatic ether, e.g. in diethyl ether, methoxybutane, dibutyl ether, tetrahydrofuran or dioxane.

Starting substances of the formula IX in which $Y_4$ is formyl or carboxyl which is free, converted into an anhydride or esterified, are prepared, for example, in an analogous manner, such as described under process variants a) and b), starting from appropriate starting substances which have a radical $Y_4$ instead of the group $-X_1-R_2$.

Compounds obtainable according to the process can be converted into other compounds of the formula I in a customary manner.

The carboxyl group can thus be esterified in a customary manner in compounds of the formula I in which the radical $R_3$ contains carboxyl. The free or esterified carboxyl group can also be amidated in compounds of the formula I in which $R_3$ contains free or esterified carboxyl. Conversely, the esterified or amidated carboxyl group can be hydrolysed to carboxyl in compounds of the formula I in which $R_3$ contains esterified or amidated carboxyl.

Compounds of the formula I in which $X_1$ is carbonyl can also be reduced in a customary manner to the corresponding compounds of the formula I in which $X_1$ is hydroxymethylene, for example as described under process variant f). In an analogous manner, resulting compounds of the formula I in which $X_1$ is hydroxymethylene can also be reduced to the corresponding compounds of the formula I in which $X_1$ is methylene.

In resulting compounds of the formula I in which $X_1$ is ketalized carbonyl, the carbonyl group can be liberated in a customary manner, for example by acid treatment. Conversely, carbonyl $X_1$ can be ketalized by reaction with an appropriate alcohol, such as a lower alkanol or a lower alkanediol.

In resulting compounds of the formula I in which $R_4$ is hydrogen, a radical $R_4$ which is other than hydrogen can also be introduced, lower alkyl, for example, by customary alkylation and, if desired as indicated, substituted alkanoyl by customary acylation. Conversely, in resulting compounds of the formula I in which $R_4$ is lower alkyl, in particular methyl, the lower alkyl group can be removed by treatment with a haloformic acid ester, such as methyl haloformate.

Likewise, in resulting compounds of the formula I in which $R_4$ is trifluoroacetyl, the trifluoroacetyl group can be removed in a customary manner, in particular by treating with a di-light metal hydride, for example with sodium borohydride in a lower alkanol, such as methanol.

Resulting salts can be converted into the free compounds in a manner known per se, e.g. by treating with a base, such as an alkali metal hydroxide, a metal carbonate or hydrogencarbonate, or another salt-forming base mentioned at the beginning, or with an acid, such as a mineral acid, e.g. with hydrochloric acid, or another salt-forming acid mentioned at the beginning.

Resulting salts can be converted into other salts in a manner known per se, acid addition salts, for example, by treating with a suitable metal salt, such as a sodium, barium or silver salt, of another acid in a suitable solvent in which an inorganic salt formed is insoluble and thus precipitates from the reaction equilibrium, and base salts by liberation of the free acid and fresh salt formation.

The compounds of the formula I, including their salts, can also be obtained in the form of hydrates or include the solvent used for crystallization.

As a result of the close relationship between the novel compounds in free form and in the form of their salts, hereinbefore and hereinafter the free compounds and their salts are analogously and expediently to be understood as also meaning, where appropriate, the corresponding salts or free compounds.

Resulting diastereomer mixtures and racemate mixtures can be separated into the pure diastereomers or racemates in a known manner on the basis of the physicochemical differences of the constituents, for example by chromatography and/or fractional crystallization.

Resulting racemates can also be resolved into the optical antipodes by known methods, for example by recrystallization from an optically active solvent, with the aid of microorganisms or by reaction of the resulting diastereomer mixture or racemate with an optically active auxiliary compound, e.g. corresponding to the acidic, basic or functionally modifiable groups contained in compounds of the formula I, with an optically active acid, base or an optically active alcohol, into mixtures of diastereomeric salts or functional derivatives, such as esters and separation thereof into the diastereomers, from which the enantiomers desired in each case can be set free in the manner customary in each case. Bases, acids and alcohols suitable for this purpose, are, for example, optically active alkaloid bases, such as strychnine, cinchonine or brucine, or D- or L-(1-phenyl) ethylamine, 3-pipecoline, ephedrine, amphetamine and similar synthetically accessible bases, optically active carboxylic or sulfonic acids, such as quinic acid or D- or L-tartaric acid, D- or L-di-o-toluyltartaric acid, D- or L-malic acid, D- or L-mandelic acid, or D- or L-camphorsulfonic acid, or optically active alcohols, such as borneol or D- or L-(1-phenyl)ethanol.

The invention also relates to those embodiments of the process according to which a compound obtainable from any stage of the process as an intermediate is used as a starting compound and the missing steps are carried out or a starting substance is used in the form of a salt or, in particular, formed under the reaction conditions.

The novel starting substances, which were especially developed for the preparation of the compounds according to the invention, in particular the choice of starting substance leading to the compounds of the formula I characterized as preferred at the beginning, the processes for their preparation and their use as intermediates also form a subject of the invention.

The invention likewise relates to pharmaceutical preparations which contain compounds according to the invention or pharmaceutically acceptable salts [including those of the compound (2R*,4S*)-N-[1-(3,5-bistrifluoromethylbenzoyl)-2-(4-nitrobenzyl)piperidin-4-yl]-acetamide] thereof as active ingredients, and processes for their preparation. The novel compounds of the formula I can be used, for example, in the form of pharmaceutical preparations which contain a therapeutically effective amount of the active substance, if appropriate together with inorganic or organic, solid or liquid, pharmaceutically acceptable excipients which are suitable for enteral, e.g. oral, or parenteral administration. Tablets or gelatin capsules are thus used which contain the active ingredient together with diluents, e.g. lactose, dextrose, sucrose mannitol, sorbitol, cellulose and/or lubricants, e.g. siliceous earth, talc, stearic acid or salts thereof, such as magnesium or calcium stearate, and/or polyethylene glycol. Tablets can likewise contain binders, e.g. magnesium aluminium silicate, starches, such as maize, wheat, rice or arrowroot starch, gelatin, tragacanth, methylcellulose, sodium carboxymethylcellulose and/or polyvinylpyrrolidone, and, if desired, disintegrants, e.g. starches, agar, alginic acid or a salt thereof, e.g. sodium alginate, and/or effervescent mixtures, or absorbents, colourants, flavourings and sweeteners. The novel compounds of the formula I can also be used in the form of parenterally administerable preparations or of infusion solutions. Such solutions are preferably isotonic aqueous solutions or suspensions, it being possible to prepare these before use, for example in the case of lyophilized preparations which contain the active substance on its own or together with a carrier, e.g. mannitol. The pharmaceutical preparations can be sterilized and/or contain excipients, e.g. preservatives, stabilizers, wetting agents and/or emulsifiers, solubilizers, salts for regulating the osmotic pressure and/or buffers. The present pharmaceutical preparations, which, if desired, can contain other pharmacologically active substances, are prepared in a manner known per se, for example by means of conventional mixing, granulating, sugar-coating, dissolving or lyophilizing processes and contain from approximately 0.1% to 100%, in particular from approximately 1% to approximately 50%, and lyophilisates up to approximately 100%, of the active substance.

The invention likewise relates to the use of the compounds of the formula I including the compound (2R*,4S*)-N-[1-(3,5-bistrifluoromethylbenzoyl)-2-(4-nitrobenzyl)piperidin-4-yl]-acetamide, preferably in the form of pharmaceutical preparations. The dose can depend on various factors, such as the manner of administration, species, age and/or state of the individual. In the case of oral administration, the doses to be administered daily are between approximately 1 and approximately 50 mg/kg and, for warm-blooded animals having a body weight of approximately 70 kg, preferably between approximately 80 mg and approximately 250 mg.

The following examples serve to illustrate the invention; temperatures are stated in degrees Celsius, pressures in mbar.

EXAMPLE 1

Methyl (2R,4S)-2-[2-benzyl-1-(3,5-bistnifluoromethylbenzoyl)piperidin-4-yl-amino]acetate and methyl (2R,4S)-2-{[2-benzyl-1-(3,5-bistrifluoromethylbenzoyl)piperidin-4-yl]methoxycarbonylmethyamino}acetate

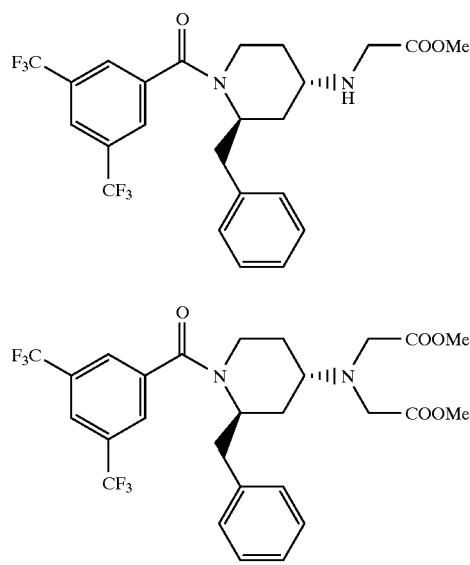

800 mg (5.23 mmol) of methyl 2-bromoacetate are added at room temperature to a solution of 1.5 g (3.49 mmol) of (2R,4S)-4-amino-2-benzyl-1-(3,5-bistrifluoromethylbenzoyl)-piperidine in 4 ml of tetrahydrofuran. After 105 minutes, 353 mg (3.49 mmol) of triethylamine are added to the yellowish solution and the suspension is stirred at room temperature for a further 16 hours. The reaction mixture is evaporated on a rotary evaporator, the residue is taken up in methylene chloride, and the solution is washed with aqueous sodium hydrogencarbonate solution, dried over sodium sulfate and evaporated on a rotary evaporator. The crude product is chromatographed on silica gel using ethyl acetate/hexane (1:3). The title compounds are each obtained as colourless oils. TLC: methylene chloride/methanol/conc. ammonia (95:4.5:0.5) $R_f$=0.55 and $R_f$=0.90. FD-MS: M$^+$=353 und 574.

EXAMPLE 2

(2R,4S)-2-[2-Benzyl-1-(3,5-bistrifluoromethylbenzoyl)piperidin-4-ylamino]-acetamide hydrochloride

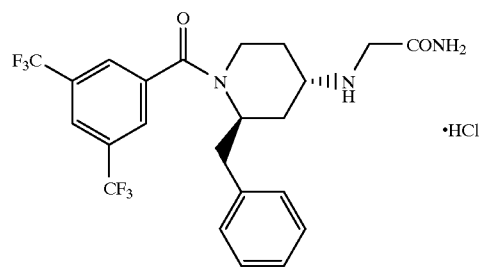

Ammonia gas is passed into a solution of 350 mg (0.696 mmol) of methyl (2R,4S)-2-[2-benzyl-1-(3,5-bistrifluoromethylbenzoyl)piperidin-4-ylamino]acetate in 5 ml of methanol at 0° C. for 10 minutes and the reaction mixture is allowed to stand at room temperature for 60 hours. The reaction mixture is evaporated on a rotary evaporator, and the residue is chromatographed on silica gel using methylene chloridelmethanol/conc. ammonia (92:7.2:0.8). The title compound crystallizes as the hydrochloride from toluene/ether. M.p. 130–133° C.; TLC: methylene chloride/methanol/conc. ammonia (90:9:1) $R_f$=0.36, FD-MS: M$^+$=487.

EXAMPLE 3

(2R,4S)-2-{[2-Benzyl-1-(3,5-bistrifluoromethylbenzoyl)piperidin-4-yl]-carbamoylmethylamino}acetamide

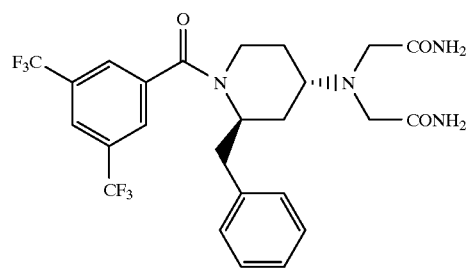

Analogously to Example 2, 350 mg (0.61 mmol) of methyl (2R,4S)-2-{[2-benzyl-1-(3,5-bistrifluoromethylbenzoy)piperidin-4-yl]methoxycarbonylmethylamino}acetate in 5 ml of methanol are treated with ammonia gas. The crude product is chromatographed on silica gel using methylene chloride/methanol/conc. ammonia (90:9:1). The title compound is obtained as white crystals. M.p.: 96–98° C. TLC: methylene chloride/methanol/conc. ammonia (90:9:1) $R_f$=0.21, FD-MS: M$^+$=544; $[\alpha]_D$=+8.7 degrees (c=1, methylene chloride).

EXAMPLE 4

(2R,4S)-2-[2-Benzyl-1-(3,5-bistrifluoromethylbenzoyl)piperidin-4-ylamino]acetic acid

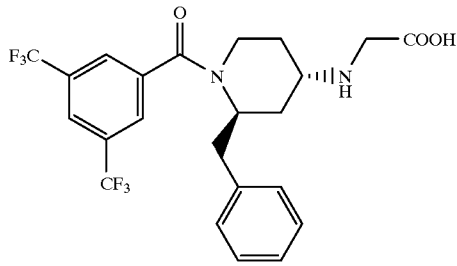

A solution of 350 mg (0.70 mmol) of methyl (2R,4S)-2-[2-benzyl-1-(3,5-bistrifluoromethyl-benzoyl)piperidin-4-ylamino]acetate in 5 ml of tetrahydrofuran is stirred intensively at room temperature with 5 ml of a 1N aqueous sodium hydroxide solution for 2 hours. The tetrahydrofuran is evaporated on a rotary evaporator, and the reaction mixture is adjusted to pH 7.4 using hydrochloric acid and extracted with methylene chloride and ethyl acetate. The title compound crystallizes from ethyl acetate/hexane. M.p.: 199–201° C. TLC: methylene chloride/methanol/acetic acid (80:18:2) $R_f$=0.19, FD-MS: $M^+$=488.

EXAMPLE 5

(2R,4S)-2-[2-Benzyl-1-(3,5-bistrifluoromethylbenzoyl)piperidin-4-ylamino]-N-(2-dimethylaminoethyl)acetamide

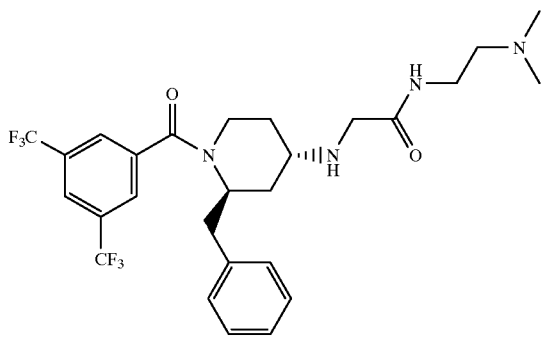

147 mg (0.58 mmol) of bis(2-oxo-3-oxazolidinyl)phosphinoyl chloride are added to a solution of 256 mg (0.52 mmol) of (2R,4S)-2-[2-benzyl-1-(3,5-bistrifluoromethylbenzoyl)piperidin-4-ylamino]acetic acid and 51 mg (0.58 mmol) of 2-dimethylaminoethylamine in 23 ml of methylene chloride and the reaction mixture is stirred at room temperature for 18 hours. It is then diluted with methylene chloride, and the organic phase is extracted with aqueous 1N potassium carbonate solution, dried over sodium sulfate and evaporated to dryness. The crude product is chromatographed on silica gel using methylene chloride/methanol/conc. ammonia (90:9:1). The title compound is obtained as a yellow oil. TLC: methylene chloride/methanol/conc. ammonia (90:9:1) $R_f$=0.23, FD-MS: $M^+$=558.

EXAMPLE 6 tert-Butyl (2R,4S)-N-{[2-benzyl-1-(3,5-bistrifluoromethylbenzoyl)piperidin-4-yl-carbamoyl]methyl}carbamate

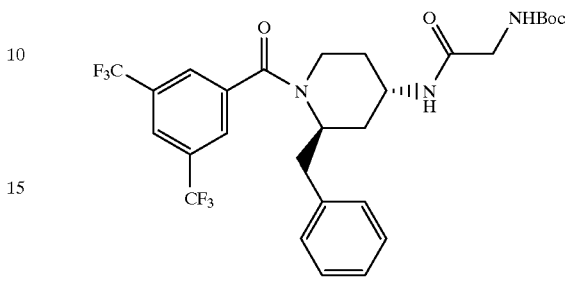

Analogously to Example 5, 400 mg (0.93 mmol) of (2R,4S)-4-amino-2-benzyl-1-(3,5-bis-trifluoromethylbenzoyl)piperidine in 10 ml of methylene chloride are reacted with 285 mg (1.1 mmol) of bis(2-oxo-3-oxazolidinyl)phosphinoyl chloride, 206 mg (2.04 mmol) of triethylamine and 179 mg (1.02 mmol) of N-tert-butoxycarbonylglycine. The title compound is obtained as a yellow oil. TLC: methylene chloride/methanol/conc. ammonia (90:9:1) $R_f$=0.57, FD-MS: $M^+$=587.

EXAMPLE 7

(2R,4S)-2-Amino-N-[2-benzyl-1-(3,5-bistrifluoromethylbenzoyl)piperidin-4-yl]-acetamide hydrochloride

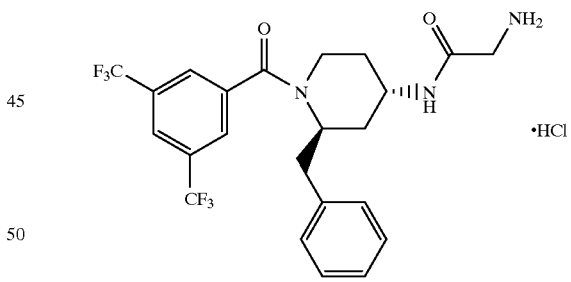

325 mg (0.533 mmol) of tert-butyl (2R,4S)-N-{[2-benzyl-1-(3,5-bistrifluoromethylbenzoyl)-piperidin-4-ylcarbamoyl]methyl}carbamate in 5 ml of trifluoroacetic acid are stirred for 30 minutes. The trifluoroacetic acid is evaporated on a rotary evaporator, the reaction mixture is taken up in methylene chloride, and the solution is extracted with 2N aqueous potassium carbonate solution, dried over magnesium sulfate and evaporated to dryness. The residue is dissolved in ethyl acetate and treated with a solution of hydrogen chloride in ether. The title compound crystallizes in white needles. M.p.: 137–140° C.; TLC: methylene chloride/methanol/conc. ammonia (90:9:1) $R_f$=0.35, FAB-MS: $M^+$=487.

EXAMPLE 8 tert-Butyl (2R,4S)-2-[2-benzyl-1-(3,5-bistrifluoromethylbenzoyl)piperidin-4-yl-amino]acetate hydrochloride and tert-butyl (2R,4S)-2-{[2-benzyl-1-(3,5-bistrifluoromethylbenzoyl)piperidin-4-yl]tert-butoxcarbonylmethylamino}acetate hydrochloride

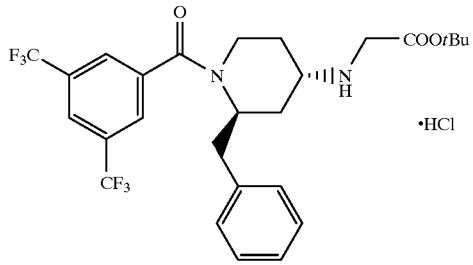

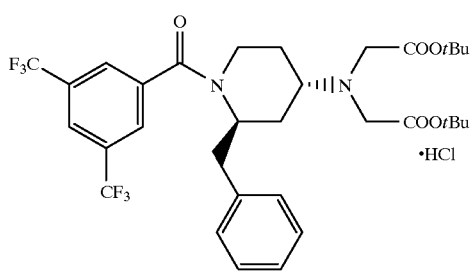

Analogously to Example 1, 400 mg (0.929 mmol) of (2R, 4S)-4-amino-2-benzyl-1-(3,5-bis-trifluoromethylbenzoyl) piperidine are reacted with 290 mg (1.49 mmol) of tert-butyl 2-bromoacetate and 94 mg (0.929 mmol) of triethylamine in 4 ml of tetrahydrofuran. The hydrochlorides of the title compounds are each obtained as white crystals. M.p.: 175–177° C. and 85–87° C.; TLC: hexane/ethyl acetate (1:1) $R_f$=0.44 and $R_f$=0.87. FD-MS: $M^+$=544 and 658.

EXAMPLE 9

Isopropyl (2R,4S)-2-[2-benzyl-1-(3,5-bistrifluoromethylbenzoyl)piperidin-4-yl-amino]acetate hydrochloride and isopropyl (2R,4S)-2-{[2-benzyl-1-(3,5-bistrifluoromethylbenzoyl)piperidin-4-yl]isopropoxycarbonylmethylamino}acetate hydrochloride

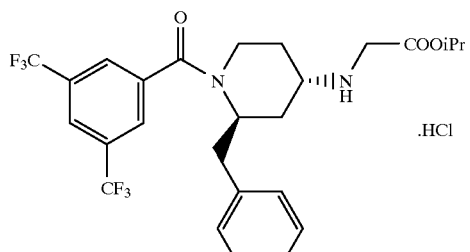

-continued

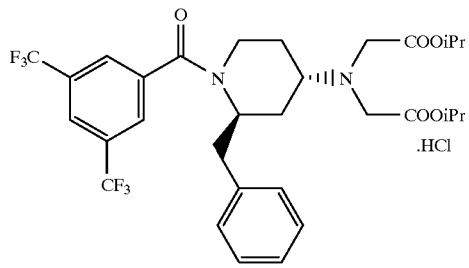

Analogously to Example 1 402 mg (0.934 mmol) of (2R, 4S)-4-amino-2-benzyl-1-(3,5-bistrifluoromethylbenzoyl) piperidine are reacted with 270 mg (1.49 mmol) of isopropyl 2-bromoacetate and 95 mg (0.934 mmol) of tnethylamine in 4 ml of tetrahydrofuran. The hydrochlorides of the title compounds are each obtained as white crystals. M.p.: 179–181° C. and 90–92° C.; TLC: hexan/ethyl acetate (1:1) $R_f$=0.41 and $R_f$=0.79. FD-MS: $M^+$=530 and 630.

EXAMPLE 10

N-Isopropyl (2R,4S)-2-[2-benzyl-1-(3,5-bistrifluoromethylbenzoyl)piperidin-4-yl-aminolacetamide and N-isopropyl (2R,4S)-2-[[2-benzyl-1-(3,5-bistrifluoromethylbenzoyl)-piperidin-4-yl]-(N-isopropylcarbamoylmethyl)amino]acetamide

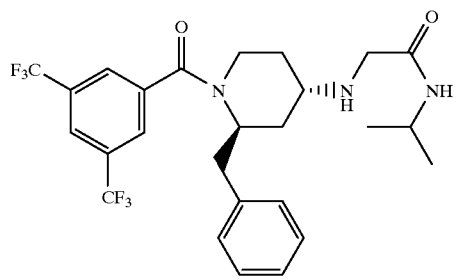

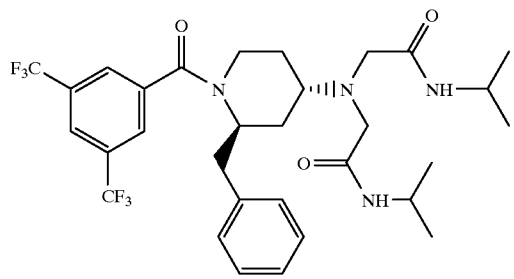

Analogously to Example 1, 391 mg (0.908 mmol) of (2R, 4S)-4-amino-2-benzyl-1-(3,5-bis-trifluoromethylbenzoyl) piperidine are reacted with 245 mg (1.36 mmol) of 2-bromo-N-isopropylacetamide and 114 mg (1.36 mmol) of sodium hydrogencarbonate in 4 ml of acetonitrile. The title compounds are each obtained as white crystals. M.p.: 115–116° C. and 156–158° C. TLC: methylene chloride/methanol/conc. ammonia (90:9:1) $R_1$=0.44 and $R_1$=0.51. FD-MS: $M^+$=529 and 628.

EXAMPLE 11
2-Ethoxyethyl (2R,4S)-2-[2-benzyl-1-(3,5-bistdfluoromethylbenzoyl)piperidin-4-ylamino]acetate and 2-ethoxyethyl (2R,4S)-N-[[2-benzyl-1-(3,5-bistrifluoromethylbenzoyl)-piperidin-4-yl]-(N-(2-ethoxyethoxycarbonylmethyl))amino]acetate

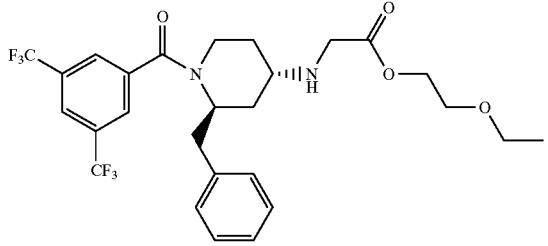

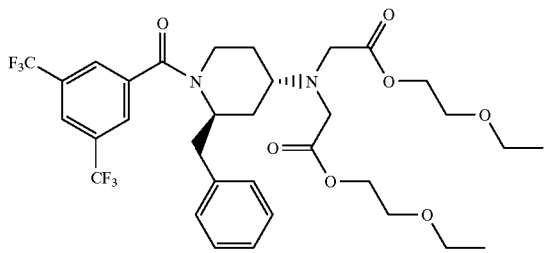

Analogously to Example 1, 427 mg (0.993 mmol) of (2R, 4S)-4-amino-2-benzyl-1-(3,5-bis-trifluoromethylbenzoyl)piperidine are reacted with 265 mg (1.59 mmol) of 2-ethoxyethyl 2-chloroacetate and 686 mg (4.97 mmol) of potassium carbonate in 5 ml of dioxane. The title compounds are each obtained as yellow oils. TLC: methylene chloride/acetone (100:5) $R_f$=0.09 and $R_f$=0.43. FD-MS: $M^+$=560 and 690.

EXAMPLE 12
(2R,4S)-N-[2-Benzyl-1-(3,5-bistrifluoromethylbenzoyl)piperidin-4-yl]-2-dimethylaminoacetamide

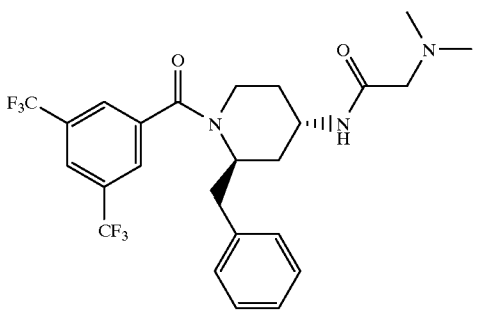

Analogously to Example 5,168 mg (0.391 mmol) of (2R, 4S)-4-amino-2-benzyl-1-(3,5-bistrifluoromethylbenzoyl)piperidine in 5 ml of methylene chloride are reacted with 109 mg (0.43 mmol) of bis(2-oxo-3-oxazolidinyl)phosphinoyl chloride, 119 mg (1.18 mmol) of triethylamine and 44 mg (0.43 mmol) of N,N-dimethylglycine. The hydrochloride of the title compound is obtained as white crystals. M.p.: 233–238° C.; TLC: methylene chloride/methanol/conc. ammonia (90:9:1) $R_f$=0.61, FD-MS: $M^+$=515.

EXAMPLE 13
(2R,4S)-2-[2-Benzyl-1-(3,5-bistrifluoromethylbenzoyl)piperidin-4-ylamino]-N,N-dimethyl acetamide hydrochloride and (2R,4S)-2-{[2-benzyl-1-(3,5-bistrifluoromethylbenzoyl)piperidine-4-yl]dimethylcarbamoylmethylamino}-N,N-dimethylacetamide

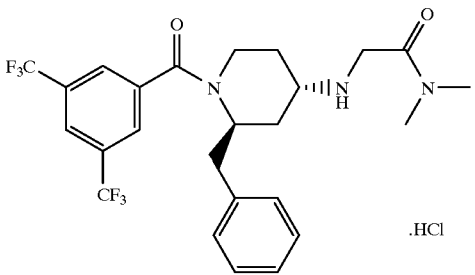

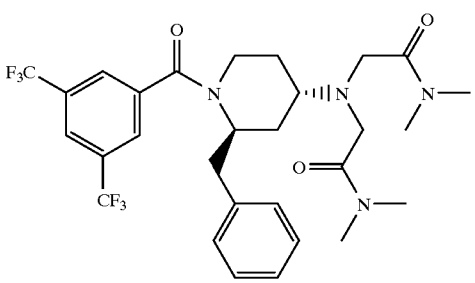

Analogously to Example 1, 434 mg (1.01 mmol) of (2R, 4S)-4-amino-2-benzyl-1-(3,5-bistrifluoromethylbenzoyl)piperidine are reacted with 195 mg (1.61 mmol) of 2-chloro-N,N-dimethylacetamide and 1.11 g (8.05 mmol) of potassium carbonate in 5 ml of dioxane. The title compounds are obtained as white crystals or as a white foam. M.p.: 127–130° C.; TLC: methylene chloride/methanol/conc. ammonia (90:9:1) $R_f$=0.49 and $R_f$=0.56. FD-MS: $M^+$=515 and 600.

EXAMPLE 14
(2R,4S)-N-[2-Benzyl-1-(3,5-bistrifluormethylbenzoyl)piperidin-4-yl]-2-(morpholin-4-yl)acetamide

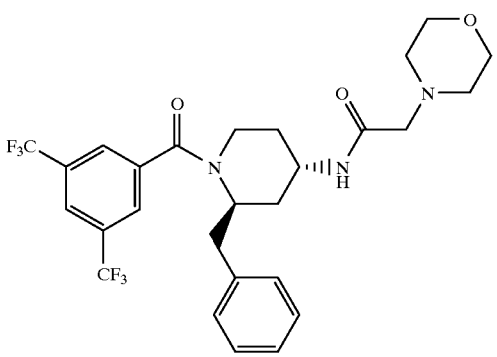

Analogously to Example 5, 215 mg (0.50 mmol) of (2R, 4S)-4-amino-2-benzyl-1-(3,5-bistrifluoromethylbenzoyl)piperidine in 2 ml of dioxane are reacted with 178 mg (0.70 mmol) of bis(2-oxo-3-oxazolidinyl)phosphinoyl chloride, 400 mg (4 mmol) of triethylamine and 109 mg (0.75 mmol) of morpholin-4-ylacetic acid, prepared from 69.7 mg (0.8 mmol) of morpholine and 104 mg (0.75 mmol) of bromoacetic acid. The title compound crystallizes from hexane/ether in white needles. M.p.: 116–120° C.; TLC: methylene chloride/methanol/conc. ammonia (95:4.5:0.5) $R_f$=0.39, FD-MS: $M^+$=557.

EXAMPLE 15

Cyclohexyl (2R,4S)-2-[2-benzyl-1-(3,5-bistrifluoromethylbenzoyl)piperidin-4-ylaminol-acetate hydrochloride and cyolohexyl (2R,4S)-2-{r2-benzyl-1-(3,5-bistrifluoromethyl-benzoyl)piperidin-4-yl]-N-(cyclohexyloxycarbonylmethyl)amino}acetate hydrochloride

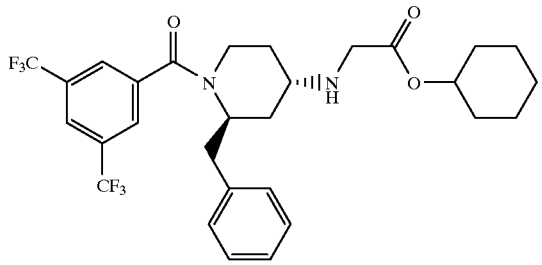

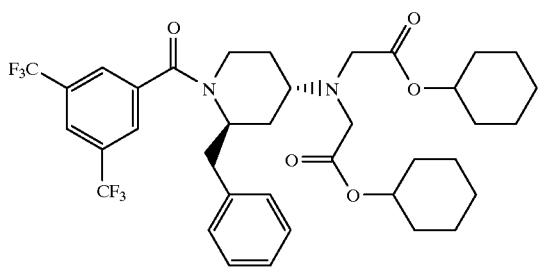

Analogously to Example 1, 427 mg (0.993 mmol) of (2R, 4S)-4-amino-2-benzyl-1-(3,5-bis-trifluoromethylbenzoyl) piperidine are reacted with 298 mg (1.69 mmol) of cyclohexyl 2-chloroacetate and 700 mg (5.07 mmol) of potassium carbonate in 5 ml of dioxane. The hydrochlorides of the title compounds are each obtained as white crystals. M.p.: 172–174° C. and 185–190° C.; TLC: methylene chloride/acetone (10:1) $R_f$=0.08 and $R_f$=0.43. FD-MS: M$^+$570 and 710.

EXAMPLE 16

(2R,4S)-4-Amino-2-benzyl-1-(3,5-bistrifluoromethylbenzoyl)-N-(3-dimethylaminopropyl) piperidine dihydrochloride and 3-dimethylaminopropyl (2R, 4S)-N-[2-benzyl-1-(3,5-bistrifluoromethylbenzoyl) piperidin-4-yl]carbamate

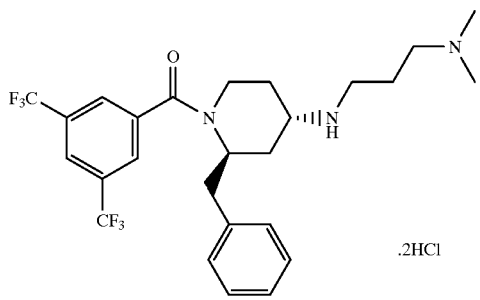

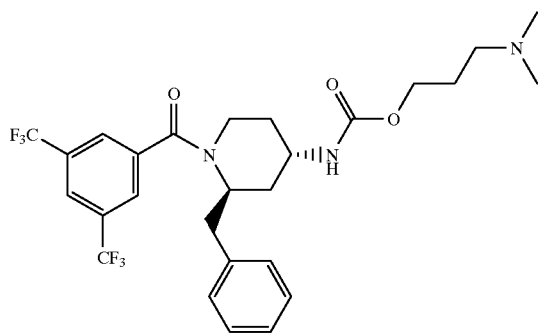

Analogously to Example 1, 432 mg (1.00 mmol) of (2R, 4S)-4-amino-2-benzyl-1-(3,5-bistrifluoromethylbenzoyl) piperidine are reacted with 286 mg (1.81 mmol) of 1-chloro-3-dimethylaminopropane hydrochloride and 793 mg (5.74 mmol) of potassium carbonate in 5 ml of acetonitrile. The title compounds are obtained as white crystals, m.p.: 198–202° C., or as a white foam; TLC: methylene chloride/methanol/conc. ammonia (85:13.5:1.5) $R_f$=0.18 and $R_f$=0.39. FD-MS: M$^+$=515 and 559.

EXAMPLE 17

(2R,4S)-2-Benzyl-1-(3,5-bistrifluoromethylbenzoyl)-4-morpholin-4-ylpiperidine

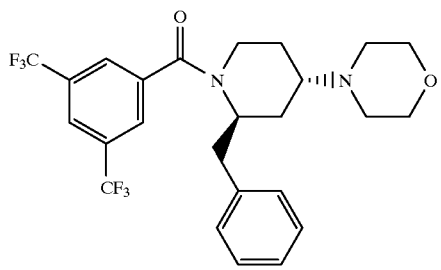

342 mg (2.39 mmol) of 2,2'-dichlorodiethyl ether and 750 mg (5.43 mmol) of potassium carbonate are added to a solution of 234 mg (0.544 mmol) of (2R,4S)-4-amino-2-benzyl-1-(3,5-bistrifluoromethylbenzoyl)piperidine in 30 ml of dioxane and the mixture is stirred at 120° C. in a pressure tube for 14 days. The solid is then filtered, the filtrate is diluted with methylene chloride, and the organic phase is extracted with aqueous 1N potassium carbonate solution, dried over sodium sulfate and evaporated to dryness. The crude product is chromatographed on silica gel using ethyl acetate/acetone (95:5). The title compound is obtained as a white foam. TLC: methylene chloridelmethanol/conc. ammonia (90:9:1) $R_f$=0.53, FD-MS: M$^+$=500.

EXAMPLE 18
(2R,4S)-4-Amino-2-benzyl-1-(3,5-bistrifluoromethylbenzoyl)-N-isobutyl-4-piperidine hydrochloride and isobutyl (2R,4S)-N-[2-benzyl-1-(3,5-bistrifluoromethylbenzoyl)pipedidin-4-yl]carbamate

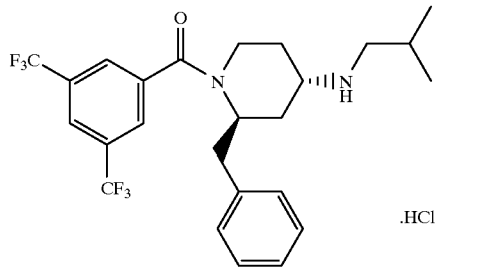

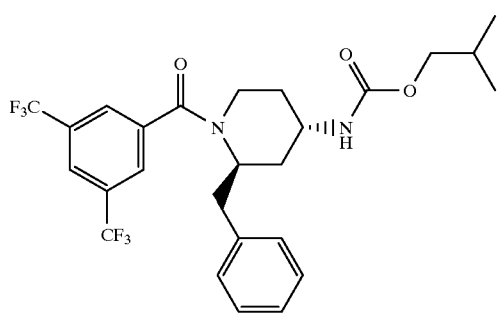

Analogously to Example 1, 404 mg (0.939 mmol) of (2R,4S)-4-amino-2-benzyl-1-(3,5-bistrifluoromethylbenzoyl)piperidine are reacted with 220 mg (1.60 mmol) of isobutyl bromide and 1.2 g (8.5 mmol) of potassium carbonate in 5 ml of dioxane. The title compounds are obtained as light brown foams: TLC: ether/hexane (3:1) $R_f$=0.14 and $R_f$=0.48. FD-MS: M$^+$=486 and 530.

EXAMPLE 19
(2R,4S)-4-Amino-2-benzyl-1-(3,5-bistrifluoromethylbenzoyl)-N-(2,2-dimethylpropyl)piperidine hydrochloride

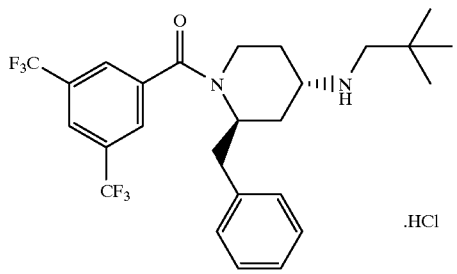

111 mg (1.3 mmol) of pivalaldehyde and 500 mg of magnesium sulfate are added to a solution of 429 mg (0.997 mmol) of (2R,4S)-4-amino-2-benzyl-1-(3,5-bistrifluoromethylbenzoyl)piperidine in 1 ml of methylene chloride and the mixture is stirred at room temperature for 18 hours. It is then filtered, the filtrate is concentrated on a rotary evaporator and the residue is dissolved in methanol. 50 mg (1.3 mmol) of sodium borohydride are added at 0° C. and the mixture is stirred for 1 hour. It is then treated with acetone, subsequently stirred for 1 hour and evaporated to dryness on a rotary evaporator. The crude product is chromatographed on silica gel using ether/hexane (3:1). After treating with an ethereal hydrogen chloride solution, the title compound is obtained as a light brown foam. TLC: ether/hexane (3:1) $R_f$=0.37, FD-MS: M$^+$=500.

EXAMPLE 20
2-Methoxyethyl (2R,4S)-2-[2-benzyl-1-(3,5-bistrifluoromethylbenzoyl)piperidin-4-ylamino]acetate and 2-methoxyethyl (2R,4S)-[[2-benzyl-1-(3,5-bistrifluoromethyl-benzoyl)pipedidin-4-yl]-N-(2-methoxyethoxycarbonylmethyl)amino]acetate

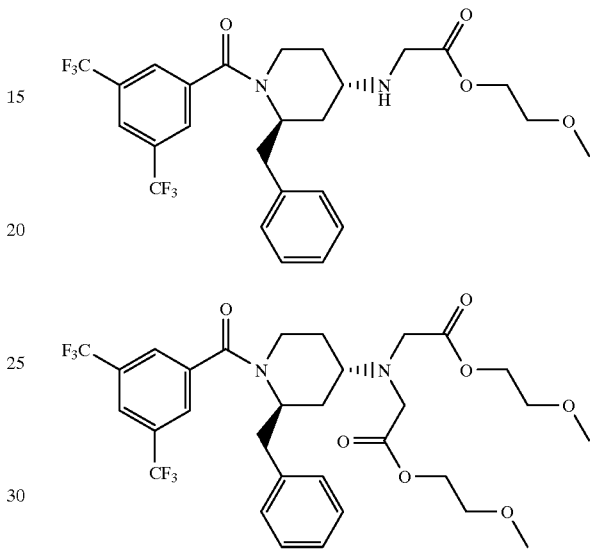

Analogously to Example 1, 442 mg (0.993 mmol) of (2R,4S)-4-amino-2-benzyl-1-(3,5-bis-trifluoromethylbenzoyl)piperidine are reacted with 282 mg (1.85 mmol) of 2-methoxyethyl chloroacetate and 700 mg (5.07 mmol) of potassium carbonate in 5 ml of dioxane. The title compounds are each obtained as brown oils. TLC: methylene chloride/acetone (3:1) $R_f$=0.33 and $R_f$=0.83. FD-MS: M$^+$=546 and 662.

EXAMPLE 21
2-Dimethylaminoethyl (2R,4S)-N-[2-benzyl-1-(3,5-bistrifluoromethylbenzoyl)-piperidin-4-yl]carbamate

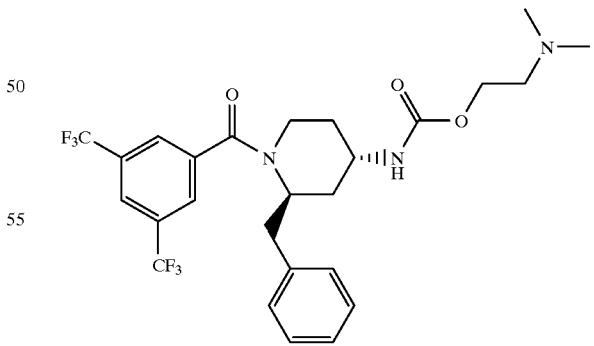

Analogously to Example 17, 403 mg (0.936 mmol) of (2R,4S)-4-amino-2-benzyl-1-(3,5-bis-trifluoromethylbenzoyl)piperidine are reacted with 230 mg (1.50 mmol) of 1-chloro-2-dimethylaminoethane hydrochloride and 647 mg (4.68 mmol) of potassium carbonate in 5 ml of dioxane in a pressure tube. The title compound is obtained as a beige foam. TLC: methylene chloride/methanol/conc. ammonia (90:9:1) $R_f$=0.49. FD-MS: $M^+$=545.

EXAMPLE 22

(2R,4S)-N-[2-Benzyl-1-(3,5-bistrifluoromethylbenzoyl)piperidin-4-yl]acetate

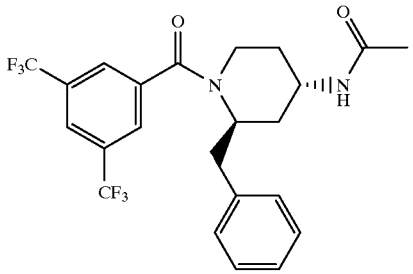

95 mg (0.934 mmol) of acetic anhydride are added to a solution of 200 mg (0.467 mmol) of (2R,4S)-4-amino-2-benzyl-1-(3,5-bistrifluoromethylbenzoyl)piperidine and 95 mg (0.934 mmol) of triethylamine in 2 ml of methylene chloride and the reaction mixture is stirred at room temperature for 2.5 hours. It is then diluted with methylene chloride, and the organic phase is extracted once with aqueous 1N sodium hydroxide solution and once with aqueous 1N hydrochloric acid, dried over sodium sulfate and evaporated to dryness. The crude product is chromatographed on silica gel using tert-butyl methyl ether/methanol/conc. ammonia (95:4.5:0.5). The title compound is obtained as a yellow oil. TLC: tert-butyl methyl ether/methanol/conc. ammonia (95:4.5:0.5) $R_f$=0.36, FD-MS: $M^+$=472.

EXAMPLE 23

(2R,4S)-N-[2-Benzyl-1-(3,5-dimethylbenzoyl)piperidin-4-yl]butyramide

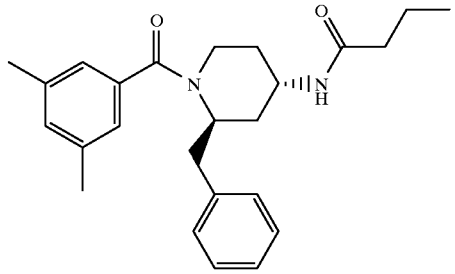

Analogously to Example 22, 200 mg (0.62 mmol) of (2R,4S)-4-amino-2-benzyl-1-(3,5-di-methylbenzoyl)piperidine (EP 532456 A) are reacted with 73 mg (0.682 mmol) of butyryl chloride and 72 mg (0.713 mmol) of triethylamine in 2 ml of tetrahydrofuran. The title compound is obtained as white crystals. M.p.: 151–154° C.; TLC: hexane/ethyl acetate (1:5) $R_f$=0.28. FD-MS: $M^+$=392.

EXAMPLE 24

(2R,4S)-N-[2-Benzyl-1-(3,5-dichlorobenzoyl)piperidin-4-yl]butyramide

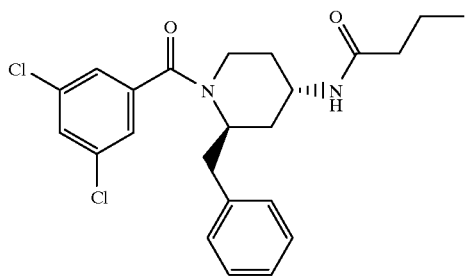

Analogously to Example 22, 200 mg (0.62 mmol) of (2R,4S)-4-amino-2-benzyl-1-(3,5-dichlorobenzoyl)piperidine (EP 532456 A) are reacted with 70 mg (0.661 mmol) of butyryl chloride and 111 mg (1.1 mmol) of triethylamine in 2 ml of methylene chloride. The title compound is obtained as white crystals. M.p.: 122° C.; TLC: hexane/ethyl acetate (1:2) $R_f$=0.24. FD-MS: $M^+$=432.

EXAMPLE 25

(2R,4S)-N-[1-(3,5-Bistrifluoromethylbenzoyl)-2-(4-chlorobenzyl)piperidin-4-yl]formamide

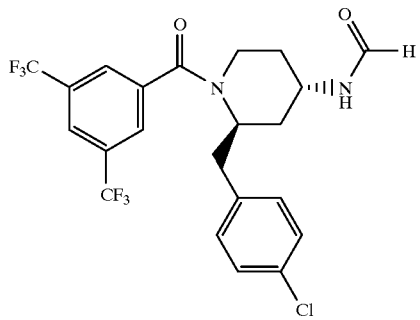

A solution of 200 mg (0.43 mmol) of (2R,4S)-1-(3,5-bistrifluoromethylbenzoyl)-2-(4-chlorobenzyl)piperidin-4-ylamine in 5 ml of butyl formate is heated to reflux for 90 minutes. After cooling, the reaction mixture is evaporated under reduced pressure. The residue is crystallized from ethyl acetate/hexane. The title compound is obtained as white crystals. M.p.: 196–198° C. TLC: methylene chloride/methanol/conc. ammonia (90:9:1) $R_f$=0.55, FD-MS: $M^+$=492; $[\alpha]^D$=−13.1 degrees (c=1, EtOH).

The starting compound for this can be prepared, for example, as follows:

a) Methyl [1-(4-chlorobenzyl)but-3-enyl]ethoxymethylcarbamate

A suspension of 10.0 g of sodium hydride (80% in mineral oil, 333 mmol) in dry THF (tetrahydrofuran) is heated to reflux under argon. A solution of 60.5 g (238 mmol) of methyl [1-(4-chlorobenzyl)but-3-enyl]carbamate in 50 ml of dry THF is added dropwise in the course of 1 hour. The mixture is then boiled under reflux for a further 2 hours until the evolution of gas subsides. The mixture is cooled to 0° C. and chloromethyl ethyl ether is added dropwise so that the reaction temperature does not rise above 5° C. After this, the mixture is slowly heated to 25° C. and stirred for 12 hours. Excess sodium hydride is cautiously destroyed with 1 ml of water before more water is added. The phases are separated and the aqueous phase is extracted again with tert-butyl methyl ether. The combined organic phases are washed with brine, dried over sodium sulfate and evaporated. The crude product is distilled at 0.1 mbar and has a boiling range of 120–125° C. TLC: ethyl acetate/hexane (1:6) $R_f$=0.34, FD-MS: M$^+$=311(313).

b) Methyl (2R*,4S*)-4-acetylamino-2-(4-chlorobenzyl) pipeidine-1-carboxylate 20.6 ml (308 mmol) of chlorosulfonic acid are initially introduced into 500 ml of acetonitrile at −40° C. A solution of 48.0 g (154 mmol) of methyl [1-(4-chlorobenzyl)but-3-enyl]ethoxymethylcarbamate in 50 ml of acetonitrile is added dropwise such that the reaction temperature does not rise beyond −10° C. The mixture is then stirred at −15° C. for a further 20 minutes before the reaction is treated with 370 ml of 2N sodium hydroxide solution and 100 ml of 10% strength aqueous sodium hydrogencarbonate solution. The phases are separated and the aqueous phase is extracted twice more with toluene. The combined organic phases are dried over sodium sulfate. The crude product is crystallized from toluene and affords the title compound as white crystals. M.p.: 169–170° C. TLC: methylene chloride/methanol/conc. ammonia (90:9:1) $R_f$=0.42, FD-MS: M$^+$=325.

c) (2R*,4S*)-N-[2-(4-Chlorobenzyl)piperidin-4-yl] acetamide

Methyl (2R*,4S*)-4-acetylamino-2-(4-chlorobenzyl) piperidine-1-carboxylate (30.0 g, 92.3 mmol) are treated with 51.8 ml 33% strength hydrogen bromide in acetic acid. After 16 hours, the mixture is treated with 200 ml of water and washed twice with toluene. The aqueous phase is rendered basic and extracted twice with ethyl acetate. The organic phases are dried on potassium carbonate and evaporated on a rotary evaporator. The title compound crystallizes from EtOHl ethyl acetate as the hydrochloride. M.p.: 288–289° C. TLC: methylene chloride/methanolconc. ammonia (90:9:1) $R_f$=0.17, FD-MS: (M+1)$^+$=267.

d) (2'S,2R,4S)-2-[4-Acetylamino-2-(4-chlorobenzyl) piperidin-1-yl]-2-oxo-1-phenylethyl acetate Racemic N-[2-(4-chlorobenzyl)piperidin-4-yl]acetamide hydrochloride (20.5 g, 67.6 mmol) is initially introduced into 34 ml of 2N sodium hydroxide solution, 150 ml of a 10% strength aqueous sodium hydrogencarbonate solution and 50 ml of methylene chloride with vigorous stirring at 0° C. S(+)-O-Acetylmandeloyl chloride [2] (14.9 g, 70 mmol) is added dropwise to this mixture during the course of 1 hour. The mixture is subsequently stirred at +4° C. for 1 hour. The phases are separated, and the organic phase is dried over sodium sulfate and evaporated on a rotary evaporator. The title compound is isolated as a pure diastereomer after crystallizing twice from methylene chloride/tert-butyl methyl ether. M.p.: 209–211° C. TLC: methylene chloride/isopropanol (9:1) $R_f$=0.65, FD-MS: M$^+$=443. $[\alpha]^D$=+77.5 degrees (c=1, methylene chloride).

The mother liquors contain mainly the non-crystalline diastereomer (2'S,2S,4R)-N-[2-(4-chlorobenzyl)-1-(acetoxyphenylacetyl)piperidin-4-yl]acetamide. TLC: methylene chloride/isopropanol (9:1) $R_f$=0.70.

e) (2R,4S)-4-Amino-1-(3,5-bistrifluoromethylbenzoyl)-2-(4-chlorobenzyl)piperidine (2'S,2R,4S)-2-[4-acetylamino-2-(4-chlorobenzyl) piperidin-1-yl]-2-oxo-1-phenylether acetate (37.4 g, 84.5 mmol) is boiled under reflux for 2 days in 370 ml of 6N hydrochloric acid. After cooling, the mixture is rendered basic with solid sodium hydroxide and extracted with methylene chloride. The combined organic phases are dried over potassium carbonate and evaporated on a rotary evaporator. The residue, consisting of almost pure (2R,4S)-4-amino-2-(4-chlorobenzyl)piperidine (19.0 g, 84.5 mmol, 100%), is treated with 8.5 ml (84.5 mmol) of benzaldehyde and the mixture is concentrated twice on a rotary evaporator using 150 ml of toluene. The oily residue is taken up in 180 ml of methylene chloride and 15.3 ml (110 mmol) of triethylamine and the solution is cooled to 10° C. Bistrifluoromethylbenzoyl chloride (25.7 g, 92.9 mmol) is added dropwise during the course of 15 minutes and the mixture is then stirred at 25° C. for 1 hour. The reaction mixture is treated with 250 ml of 1N HCl and the methylene chloride is removed under reduced pressure on a rotary evaporator. Hexane and ethanol are added until two homogeneous phases result. After separating off the organic phase, the aqueous phase is washed further with hexane until all the benzaldehyde has been removed. The mixture is rendered basic with solid sodium hydroxide and repeatedly extracted with methylene chloride. The organic phases are dried over sodium sulfonate and concentrated on a rotary evaporator. Crystallization from tert-butyl methyl ether/hexane affords the title compound as white crystals. M.p.: 79–81° C. TLC: methylene chloride/methanol/conc. ammonia (90:9:1) $R_f$=0.21, FD-MS: (M+1)$^+$=465. $[\alpha]^D$=−12.7 degrees(c=1, methylene chloride).

EXAMPLE 26

(2R,4S)-N-[1-(3,5-Bistrifluoromethylbenzoyl)-2-(4-chlorobenzyl)piperidin-4-yl]-acetamide

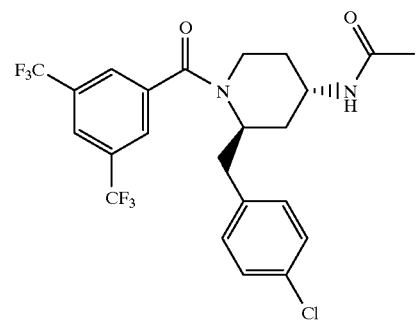

(2R,4S)-4-Amino-1-(3,5-bistrifluoromethylbenzoyl)-2-(4-chlorobenzyl)piperidine (232 mg, 0.5 mmol) is treated with 102 mg (1 mmol) of acetic anhydride in 0.5 ml of pyridine. After 1 hour, 0.5 ml of 1N sodium hydroxide solution is added and stirred for 2 hours. The mixture is taken up in ethyl acetate, washed with 1N HCl, brine and 10% aqueous sodium carbonate solution, dried over sodium sulfate and evaporated on a rotary evaporator. The crude product is crystallized from diethyl ether and affords the title compound as white crystals. M.p.: 120–123° C. TLC: methylene chloride/methanol (19:1) $R_f$=0.60, FD-MS: M$^+$=506(508). $[\alpha]^D$=−5.0 degrees (c=1, EtOH).

EXAMPLE 27

(2R,4S)-N-[1-(3,5-Bistrifluoromethylbenzoyl)-2-(4-chlorobenzyl)piperidin-4-yl]-propionamide

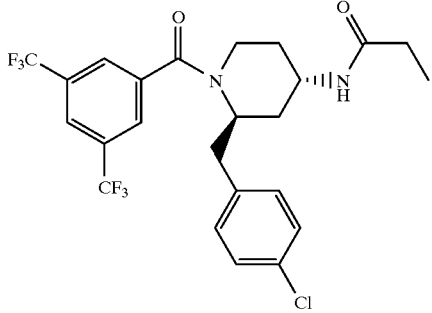

Analogously to Example 26, 232 mg (0.5 mmol) of (2R,4S)-4-amino-1-(3,5-bistrifluoromethylbenzoyl)-2-(4-chlorobenzyl)piperidine are reacted with 130 mg (1 mmol) of propionic anhydride in 0.5 ml of pyridine. The title compound is obtained as white crystals m.p.: 106–110° C. TLC: methylene chloride/methanol (19:1) $R_f$=0.50, FD-MS: $M^+$=520(522). $[\alpha]^D$=−11.3 degrees (c=1, EtOH).

EXAMPLE 28

(2R,4S)-N-[1-(3,5-Bistrifluoromethylbenzoyl)-2-(4-chlorobenzyl)piperidin-4-yl]-butyramide

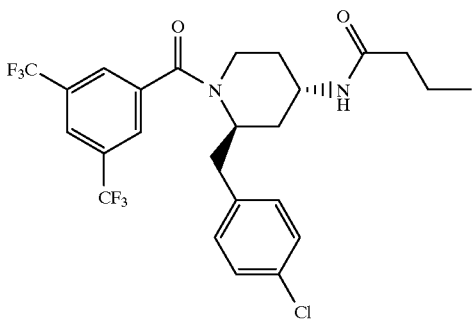

Analogously to Example 26, 232 mg (0.5 mmol) of (2R,4S)-4-amino-1-(3,5-bistrifluoromethylbenzoyl)-2-(4-chlorobenzyl)piperidine are reacted with 158 mg (1 mmol) of butyric anhydride in 0.5 ml of pyridine. The title compound is obtained as white crystals, m.p.: 143–145° C. TLC: methylene chloride/methanol (19:1) $R_f$=0.53, FD-MS: $M^+$=534(536). $[\alpha]^D$=−13.7 degrees (c=1, EtOH).

EXAMPLE 29

N-[2-Benzyl-1-(3,5-dimethylbenzoyl)piperidin-4-yl]-2,2,2-trifluoroacetamide

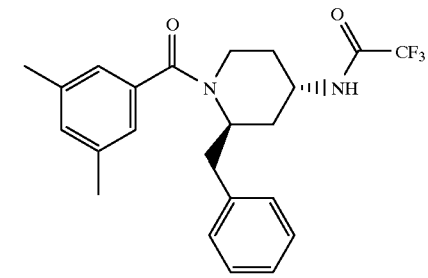

(2R,4S)-4-Amino-2-benzyl-1-(3,5-dimethylbenzoyl)piperidine (EP 532456 A) (200 mg, 0.62 mmol) are reacted with 104 mg (0.682 mmol) of trifluoroacetic anhydride in 3 ml of methylene chloride. After 2 hours, the mixture is diluted with ethyl acetate and washed with 10% strength aqueous sodium carbonate solution. The organic phase is dried over sodium sulfate and evaporated. The crude product is chromatographed on silica gel using ethyl acetate/hexane (1:2). The title compound is obtained as a yellow foam. TLC: hexane/ethyl acetate (1:1) $R_f$=0.37. FAB-MS: $(M+H)^+$=419.

EXAMPLE 30

(2R,4S)-2-Acetylamino-N-[1-(3,5-bistrifluoromethylbenzoyl)-2-(4-chlorobenzyl)-piperidin-4-yl]acetamide

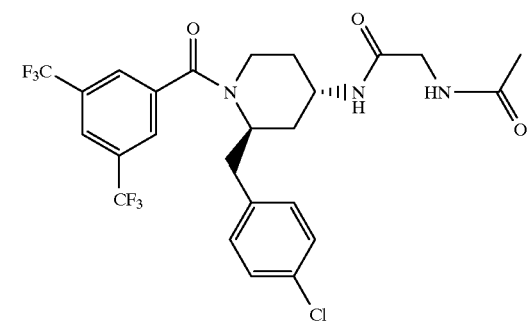

(2R,4S)-4-Amino-1-(3,5-bistrifluoromethylbenzoyl)-2-(4-chlorobenzyl)piperidine (195 mg, 0.42 mmol) is treated with 49 mg (0.42 mmol) of N-acetylglycine, 101 mg of triethylamine (1 mmol) and 117 mg (0.46 mmol) of bis(2-oxo-3-oxazolidinyl)phosphinoyl chloride in 3 ml of methylene chloride. After 48 hours, the mixture is diluted with ethyl acetate and washed with 10% strength aqueous sodium carbonate solution, 1N hydrochloric acid and brine. The organic phase is dried over sodium sulfate and concentrated on a rotary evaporator. The crude product is chromatographed on silica gel using methylene chloride/methanol (95:5). The title compound is obtained as a white lyophilizate. TLC: methylene chloride/methanol (95:5) $R_f$=0.38, FD-MS: $M^+$=563(565); $[\alpha]^D$=−6.4 degrees (c=1, EtOH).

EXAMPLE 31

Isobutyl (2R,4S)-N-[1-(3,5-bistrifluoromethylbenzoyl)-2-(4-chlorobenzyl)-piperidin-4-yl]carbamate

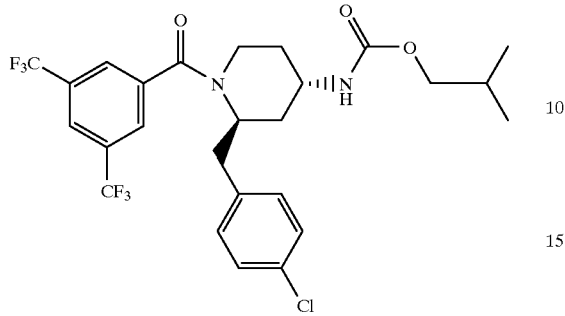

Analogously to Example 1, 250 mg (0.87 mmol) of (2R,4S)-4-amino-1-(3,5-bistrifluoromethylbenzoyl)-2-(4-chlorobenzyl)piperidine are reacted with 220 mg (1.60 mmol) of isobutyl bromide and 1.2 g (8.5 mmol) of potassium carbonate in 5 ml of dioxane. The title compound is obtained as white crystals. M.p.: 128–130° C. TLC: ethyl acetate/hexane(1:1) $R_f$=0.78, FAB-MS: (M+H)$^+$=565; [α]$^D$=–12.8 degrees (c=1, EtOH).

EXAMPLE 32

(2R,4S)-2-[1-(3,5-Bistrifluoromethylbenzoyl)-2-(4-chlorobenzyl)piperidin-4-ylamino]acetamide

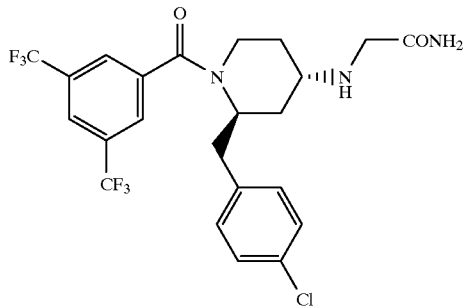

Ammonia gas is passed into a solution of 130 mg (0.24 mmol) of methyl (2R,4S)-2-[1-(3,5-bistrifluoromethylbenzoyl)-2-(4-chlorobenzyl)piperidin-4-ylamino]acetate in 5 ml of methanol at 0° C. for 10 minutes and the reaction mixture is allowed to stand at room temperature for 60 hours. Evaporation of the reaction mixture affords the title compound as a colourless oil. TLC: methylene chloride/methanol (95:5) $R_f$=0.10, FD-MS: M$^+$=521; [α]$^D$=–13.1 degrees (c=1, EtOH).

The starting compound can be prepared, for example, as follows:

Methyl (2R,4S)-2-[1-(3,5-bistrifluoromethylbenzoyl)-2-(4-chlorobenzyl)piperidin-4-ylamino]-acetate and methyl (2R,4S)-2-{[1-(3,5-bistrifluoromethylbenzoyl)-2-(4-chlorobenzyl)-piperidin-4-yl]-N-methoxycarbonylmethylamino}acetate

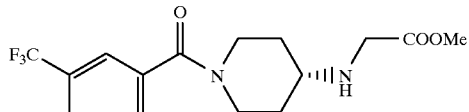

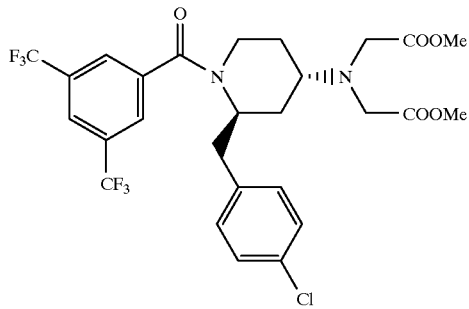

Analogously to Example 1, the title compounds are each obtained from 400 mg (0.86 mmol) of (2R,4S)-4-amino-1-(3,5-bistrifluoromethylbenzoyl)-2-(4-chlorobenzyl)-piperidine and 156 mg (1.03 mmol) of methyl bromoacetate as colourless oils. TLC: methylene chloride/methanol (95:5) $R_f$=0.75 and $R_f$=0.48. Compound with $R_f$=0.75 (methylene chloride/methanol (95:5)): $^1$H-NMR (200 MHz,CDC$_3$): δ (rotamer mixture) 7.90–7.80 (m, 1H), 7.52 (s, 1H), 7.34–7.17 (m, 4H), 6.85–6.78 (m, 1H), 5.31–5.17 (m, 0.5H), 4.80–4.67 (m, 0.5H), 3.93–3.80 (m, 0.5H), 3.70 (s, 6H, OMe), 3.64–3.54 (m, 4H, CH$_2$COOMe), 3.5–2.9 (m, 3.5H), 2.69–2.57 (m, 0.5H), 2.17–1.83 (m, 2H), 1.56–1.23 (m, 2H). Compound with $R_f$=0.48 (methylene chloride/methanol (95:5)): $^1$H-NMR (CDCl$_3$): δ (rotamer mixture) 7.90–7.80 (m, 1H), 7.55 (s, 1H), 7.37–7.13 (m, 4H), 6.88–6.80 (m, 1H), 5.34–5.18 (m, 0.5H), 4.80–4.68 (m, 0.5H), 3.92–3.77 (m, 0.5H), 3.78 (s, 3H), 3.50–3.43 (m, 2H), 3.5–2.9 (m, 3.5H), 2.68–2.55 (m, 0.5H), 2.2–1.2 (m, 4H).

EXAMPLE 33

(2R,4S)-2{[1-(3,5-Bistrifluoromethylbenzoyl)-2-(4-chlorobenzyl)piperidin-4-yl]-N-carbamoylmethylamino]acetamide

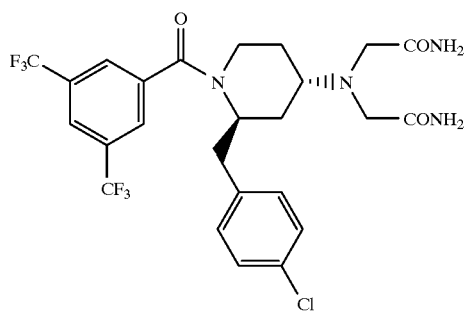

Analogously to Example 32,140 mg (0.22 mmol) of methyl (2R,4S)-2-{[1-(3,5-bistrifluoromethylbenzoyl)-2-(4-chlorobenzyl)piperidin-4-yl]-N-methoxycarbonylmethylamino}-acetate in 5 ml of methanol are treated with ammonia gas. The crude product is crystallized from diethyl ether/hexane. The title compound is obtained as white crystals. M.p.: 168–170° C. TLC: methylene chloride/methanol/conc. ammonia (90:9:1) $R_f$=0.19, FD-MS: M$^+$=578; $[\alpha]^D$=–6.4 degrees (c=1, EtOH).

EXAMPLE 34

(2R*,4S*)-N-[1-(3,5-Dimethylbenzoyl)-2-(4-nitrobenzyl)piperidin-4-yl]acetamide

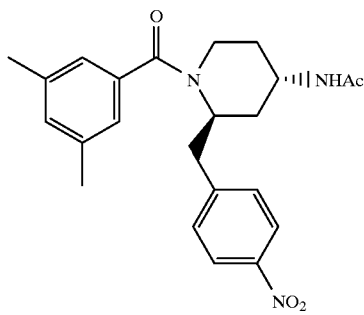

188 mg (1.11 mmol) of 3,5-dimethylbenzoyl chloride are added to a stirred suspension of 370 mg (1.11 mmol) of (2R*,4S*)-N-[2-(4-nitrobenzyl)piperidin-4-yl]acetamide in 5 ml of methylene chloride and 5 ml of 10% strength aqueous sodium hydrogencarbonate solution at 0–5° C. in the course of 1 hour. The mixture is subsequently stirred at 25° C. for 1 more hour. The organic phase is dried over sodium sulfate and evaporated. The crude product is crystallized from ethyl acetate/ether and affords the title compound as white crystals. M.p.: 198–200° C. TLC: methylene chloride/methanol (9:1) $R_f$=0.40. FD-MS: M$^+$=409.

The starting compound for this can be prepared, for example, as follows:

a) Benzyl [1-(4-nitrobenzyl)but-3-enyl]carbamate 2-(4-Nitrobenzyl)pent-4-enoic acid (9.3 g, 40.0 mmol) is treated in toluene with 11.55 g (42.0 mmol) of diphenylphosphoryl azide at 50° C. in the presence of triethylamine (5.6 ml, 40.0 mmol) and benzyl alcohol (5.18 g, 48.0 mmol). After 20 minutes, the temperature is slowly increased and the mixture is then boiled under reflux for a further 3 hours. After cooling, the reaction mixture is washed twice with 1N sodium hydroxide solution, twice with 1N hydrochloric acid and twice with brine, dried over sodium sulfate and evaporated on a rotary evaporator. The title compound is obtained as white crystals after crystallization of the crude product from toluene/hexane. M.p.: 94–95° C. TLC: ethyl acetate/hexane (1:3) $R_f$=0.22.

b) Benzyl [1-(4-nitrobenzyl)but-3-enyl]ethoxymethylcarbamate

A mixture of 10 ml of 50% strength aqueous sodium hydroxide solution, 25 ml of methylene chloride and 130 mg (0.4 mmol) of benzyltributylammonium chloride is vigorously stirred at 5–10° C. Benzyl [1-(4-nitrobenzyl)but-3-enyl]carbamate (6.8 g, 20.0 mmol) is added in one portion followed by 2.64 g (28 mmol) of chloromethyl ethyl ether over a period of 2 hours. The mixture is then stirred at room temperature for 1 hour, diluted with ice and water and extracted with methylene chloride. The organic phase is dried over sodium sulfate, evaporated and chromatographed on silica gel (hexane/ethyl acetate (10:1)). The title compound is obtained as a colourless oil. TLC: ethyl acetate/hexane (1:3) $R_f$=0.41. FD-MS: M$^+$: 398.

b) Benzyl (2R*,4S*)-4-acetylamino-2-(4-nitrobenzyl)piperidine-1-carboxylate

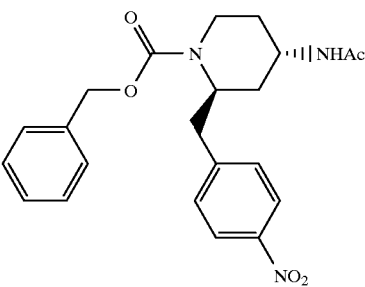

Analogously to Example 25b, 5.0 g (12.6 mmol) of benzyl [1-(4-nitrobenzyl)but-3-enyl]-ethoxymethylcarbamate are reacted with 1.77 g (25.2 mmol) of chlorosulfonic acid in acetonitrile. Chromatography on silica gel (methylene chloride/methanol 95:5) affords the title compound as a colourless resin. TLC: methylene chloride/methanol (9:1) $R_f$=0.40; FD-MS: (M+H)$^+$: 412.

c) (2R*,4S*) N-[2-(4-Nitrobenzyl)piperidin-4-yl]-acetamide

Benzyl (2R*,4S*)-4-acetylamino-2-(4-nitrobenzyl)piperidine-1-carboxylate (2.65 g, 6.45 mmol) is treated with conc. hydrochloric acid and heated at 55° C. for 2 hours, evolution of gas occurring. The reaction mixture is washed twice with hexane and evaporated under reduced pressure on a rotary evaporator. The hydrochloride of the title compound is obtained as white crystals which contain 3 molecules of water of crystallization. M.p.>250° C. TLC: methylene chloride/methanol/conc. ammonia (90:9:1) $R_f$=0.29. $^1$H-NMR (200 MHz, D$_2$O): δ 8.26 (d, 2H), 7.59 (d, 2H), 4.26–4.17 (m, 1H), 3.90–3.72 (m, 1H), 3.40–3.02(m, 4H), 1.99 (s, 3H), 2.06–1.75 (m, 4H).

EXAMPLE 35

(2R*,4S*)-N-[1-(3,5-Dimethylbenzoyl)-2-(4-cyanobenzyl)piperidin-4-yl]-acetamide

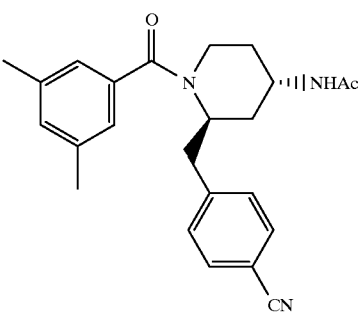

Analogously to Example 34, the title compound is obtained as white crystals. M.p.: 154–157° C.; FD-MS: M$^+$: 389.

EXAMPLE 36

(2R*,4S*)-N-[1-(3,5-Bistrifluoromethylbenzoyl)-2-(4-cyanobenzyl)piperidin-4-yl]-acetamide

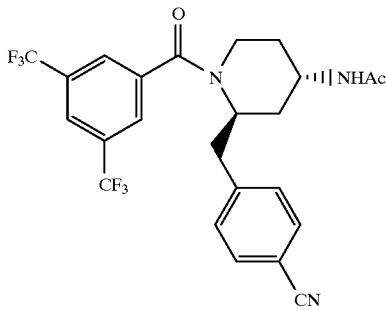

Analogously to Example 34, the title compound is obtained as a white foam. TLC: methylene chloride/methanol/conc. ammonia (90:9:1) $R_f$=0.50, FD-MS: $M^+$=497.

EXAMPLE 37

(2R*,4S*)-N-[1-(3,5-Dichlorobenzoyl)-2-(4-chlorobenzyl)piperidin-4-yl]-acetamide

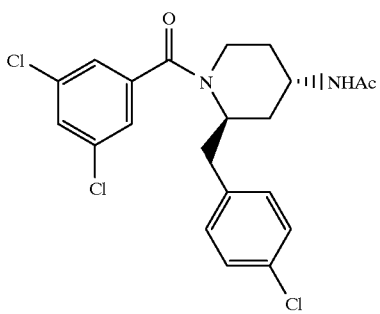

Analogously to Example 34, the title compound is obtained as white crystals. M.p.: 176–179° C. TLC: methylene chloride/methanol (19:1) $R_f$=0.37, FAB-MS: $(M+H)^+$=439.

EXAMPLE 38

(2R*,4S*)-N-[1-(3,5-Dimethylbenzoyl)-2-(4-methoxybenzyl)pipedidin-4-yl]-acetamide

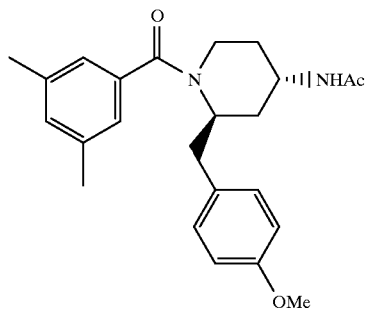

Analogously to Example 34, the title compound is obtained as white crystals. M.p.: 175–176° C. TLC: methylene chloride/methanol (9:1) $R_f$=0.54; FD-MS: $M^+$=394.

EXAMPLE 39

(2R*,4S*)-N-[1-(3,5-Bistrifluoromethylbenzoyl)-2-(3-methoxybenzyl)piperidin-4-yl]acetamide

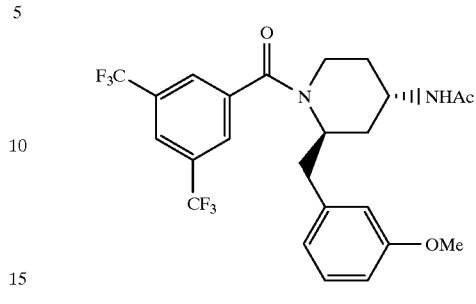

Analogously to Example 34, the title compound is obtained as a slightly coloured resin. TLC: methylene chloride/methanol (9:1) $R_f$=0.49; FD-MS: $M^+$=502.

EXAMPLE 40

(2R*,4S*)-N-[1-(3,5-Dimethylbenzoyl)-2-(4-trifluoromethylbenzyl)piperidin-4-yl]-acetamide

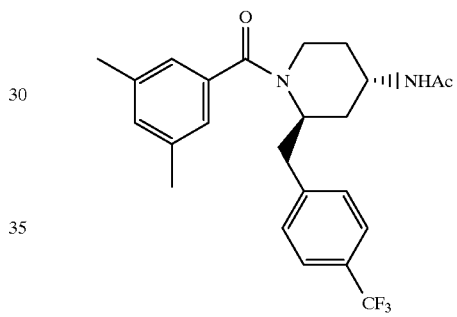

Analogously to Example 34, the title compound is obtained as white crystals. M.p.: 210–212° C. TLC: methylene chloride/methanol (9:1) $R_f$=0.46; FD-MS: $M^+$=432.

EXAMPLE 41

(2R*,4S*)-N-[1-(3,5-Dimethylbenzoyl)-2-(2,4-dichlorobenzyl)piperidin-4-yl]-acetamide

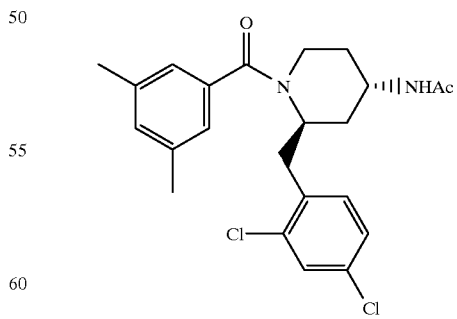

Analogously to Example 34, the title compound is obtained as white crystals. M.p.: 214–219° C. TLC: methylene chloride/methanol/conc. ammonia (90:9:1) $R_f$=0.65; FD-MS: $M^+$=432.

EXAMPLE 42
(2R*,4S*)-N-[1-(3,5-Dimethylbenzoyl)-2-(2-naphthyl)piperidin-4-yl]acetamide

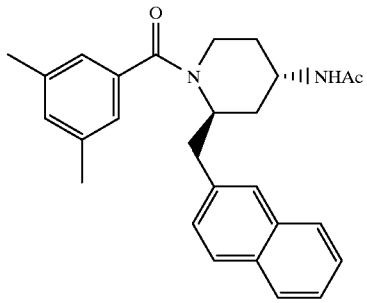

Analogously to Example 34, the title compound is obtained as white crystals. M.p.: 190–192° C. TLC: methylene chloride/methanol/conc. ammonia (90:9:1) $R_f$=0.57; FAB-MS: (M+H)$^+$=415.

EXAMPLE 43
(2R*,4S*)-N-[1-(3,5-Dimethylbenzoyl)-2-(4-iodobenzyl)piperidin-4-yl]acetamide

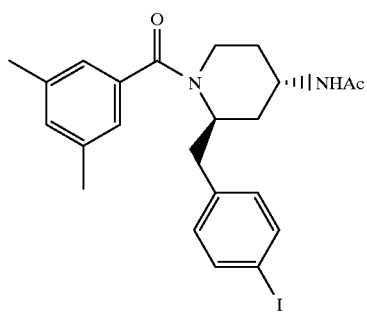

Analogously to Example 34, the title compound is obtained as a colourless resin. TLC: methylene chloride/methanol/conc. ammonia (90:9:1) $R_f$=0.50; FD-MS: (M+H)$^+$=491.

EXAMPLE 44
(2R,4S)-N-[1-(3,5-Bistrifluoromethylbenzoyl)-2-(4-chlorobenzyl)piperidin-4-yl]-pentanamide

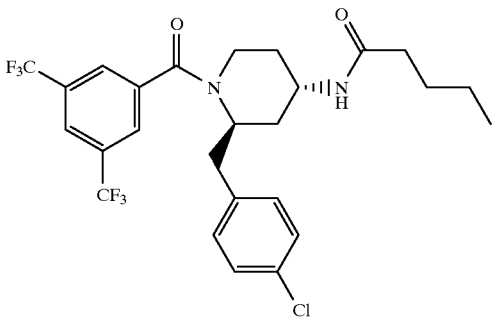

A solution of 15.0 g (32.3 mmol) of (2R,4S)-4-amino-1-(3,5-bistrifluoromethylbenzoyl)-2-(4-chlorobenzyl)piperidine (see Example 25e) in 40 ml of methylene chloride and 20 ml of 2N NaOH is cooled to 0° C. with vigorous stirring using an ice/salt bath. A solution of 3.97 g (32.94 mmol) of valeryl chloride in 3 ml of methylene chloride is rapidly added dropwise such that the reaction temperature does not exceed 5° C. The mixture is subsequently stirred for a further hour. The mixture is diluted with methylene chloride, and the aqueous phase is separated off. The organic phase is washed with 1N NaOH and dried on $Na_2SO_4$. After concentrating on a rotary evaporator, the title compound crystallizes as colourless needles from ethyl acetate/hexane. M.p.: 163–165° C. TLC: ethyl acetate $R_f$=0.67, FAB-MS: (M+H)$^+$=549, (M–H)$^-$=549. [alpha]D=–13.6 degrees (c=1, EtOH).

EXAMPLE 45
(2R,4S)-1-[1-(3,5-Bistrifluoromethylbenzoyl)-2-(4-chlorobenzyl piperidin-4-yl]-3-tert-butylurea

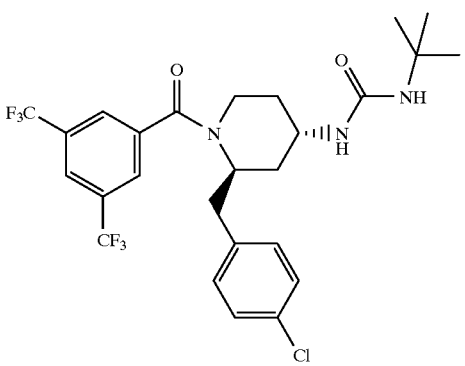

(a)

1.18 g (11.9 mmol) tert-butyl isocyanate are added dropwise at 0° C. to a solution of 5.0 g (10.8 mmol) of (2R,4S)-4-amino-1-(3,5-bistrifluoromethylbenzoyl)-2-(4-chlorobenzyl)-piperidine and 0.26 g (2.2 mmol) of 4-dimethylaminopyridine in 50 ml of tert-butyl methyl ether in the course of one minute. The mixture is then stirred at room temperature for 1 hour. The reaction mixture is diluted with tert-butyl methyl ether and washed with 1N hydrochloric acid and with brine, dried over magnesium sulfate and evaporated on a rotary evaporator. The title compound crystallizes from tert-butyl methyl ether/hexane as white crystals. M.p.:

117° C.; FD-MS: M$^+$=563 and 565; [alpha]D=–3.0 degrees (c=1, $CH_2Cl_2$).

The following can be prepared, for example, in an analogous manner:

(b) (2R,4S)-1-[1-(3,5-bistrifluoromethylbenzoyl)-2-(4-chlorobenzyl)piperidin-4-yl]-3-isopropyl-urea;

(c) (2R,4S)-1-[1-(3,5-bistrifluoromethylbenzoyl)-2-(4-chlorobenzyl)piperdin-4-yl]-3-ethylurea;

(d) (2R,4S)-1-[1-(3,5-bistrifluoromethylbenzoyl)-2-(4-chlorobenzyl)piperidin-4-yl]-3-cyclohexylurea;

(e) (2R,4S)-1-[1-(3,5-bistrifluoromethylbenzoyl)-2-(4-chlorobenzyl)piperidin-4-yl]-3-propylurea;

(f) (2R,4S)-1-[2-benzyl-1-(3,5-bistrifluoromethylbenzoyl)piperidin-4-yl]-3-cyclohexylurea (g) (2R,4S)-1-[2-benzyl-1-(3,5-bistrifluoromethylbenzoyl)piperidin-4-yl]-3-tert-butylure and (h) (2R,4S)-1-[2-benzyl-1-(3,5-bistdfluoromethylbenzoyl)pipendin-4-yl]-3-isopropylurea.

EXAMPLE 46

The following can be prepared in an analogous manner, for example as described in one of the above Examples 1–44:

n-Octyl (2R,4S)-2-[2-benzyl-1-(3,5-bistrifluoromethylbenzoyl)piperidin-4-ylamino]acetate and n-octyl (2R,4S)-2-{[2-benzyl-1-(3,5-bistrifluoromethylbenzoyl)piperidin-4-yl]-methoxycarbonylmethylamino}acetate;

n-decyl (2R,4S)-2-[2-benzyl-1-(3,5-bistrifluoromethylbenzoyl)piperidin-4-ylamino]acetate and (2R,_4S)-2-{[2-benzyl-1-(3,5-bistrifluoromethylbenzoyl)piperidin-4-yl]-methoxycarbonyl-methylamino}acetate;

n-dodecyl (2R,4S)-2-[2-benzyl-1-(3,5-bistrifluoromethylbenzoyl)piperidin-4-ylamino]acetate and n-dodecyl (2R,_4S)-2-{[2-benzyl-1-(3,5-bistrifluoromethylbenzoyl)piperidin-4-yl]-methoxycarbonylmethylamino}acetate.

EXAMPLE 47

Tablets containing, for example, 50 mg each, for example, of (2R,4S)-N-[1-(3,5-bistrifluoromethylbenzoyl)-2-(4-chlorobenzyl)piperidin-4-yl]butyramide or a salt, e.g. the hydrochloride, can be prepared as follows:

| Composition (10,000 tablets) | | |
|---|---|---|
| Active ingredient | 500.0 | g |
| Lactose | 500.0 | g |
| Potato starch | 352.0 | g |
| Gelatin | 8.0 | g |
| Talc | 60.0 | g |
| Magnesium stearate | 10.0 | g |
| Silica (highly disperse) | 20.0 | g |
| Ethanol | q.s. | |

The active ingredient is mixed with the lactose and 292 g of potato starch, and the mixture is moistened with an ethanolic solution of the gelatin and granulated through a sieve. After drying, the rest of the potato starch, the magnesium stearate, the talc and the silica are admixed and the mixture is compressed to give tablets of weight 145.0 mg each and 50.0 mg active ingredient content which, if desired, can be provided with breaking notches for finer adjustment of the dose.

EXAMPLE 48

Film-coated tablets containing, for example, 100 mg each, for example, of (2R,4S)-N-[1-(3,5-bistrifluoromethylbenzoyl)-2-(4-chlorobenzyl)piperidin-4-yl]butyramide or a salt, e.g. the hydrochloride, thereof can be prepared as follows:

| Composition (for 1,000 film-coated tablets) | | |
|---|---|---|
| Active ingredient | 100.0 | g |
| Lactose | 100.0 | g |
| Maize starch | 70.0 | g |
| Talc | 8.5 | g |
| Calcium stearate | 1.5 | g |
| Hydroxypropylmethylcellulose | 2.36 | g |
| Shellac | 0.64 | g |
| Water | q.s. | |
| Methylene chloride | q.s. | |

The active ingredient, the lactose and 40 g of the maize starch are mixed and moistened with a paste prepared from 15 g of maize starch and water (with warming), and granulated. The granules are dried, and the remainder of the maize starch, the talc and the calcium stearate are added and mixed with the granules. The mixture is pressed to give tablets (weight: 280 mg) and these are coated with a solution of the hydroxypropylmethylcellulose and of the shellac in methylene chloride; final weight of the film-coated tablet: 283 mg.

EXAMPLE 49

Hard gelatin capsules containing 100 mg of active ingredient, e.g. (2R,4S)-N-[1-(3,5-bistrifluoromethylbenzoyl)-2-(4-chlarobenzyl)piperidin-4-yl]butyramide or a salt, e.g. the hydrochloride, thereof can be prepared, for example, in the following manner:

| Composition (for 1,000 capsules) | | |
|---|---|---|
| Active ingredient | 100.0 | g |
| Lactose | 250.0 | g |
| Microcrystalline cellulose | 30.0 | g |
| Sodium lauryl sulfate | 2.0 | g |
| Magnesium stearate | 8.0 | g |

The sodium lauryl sulfate is sieved into the lyophilized active ingredient through a sieve having a mesh width of 0.2 mm. Both components are intimately mixed. Then the lactose is first sieved in through a sieve having a mesh width of 0.6 mm and then the microcrystalline cellulose is sieved in through a sieve having a mesh width of 0.9 mm. After this, the constituents are again intimately mixed for 10 minutes. Finally, the magnesium stearate is sieved in through a sieve having a mesh width of 0.8 mm. After mixing for a further 3 minutes, 390 mg each of the obtained formulation are filled into hard gelatin capsules of size 0.

EXAMPLE 50

In an analogous manner, for example as described in the above Examples 47 to 49, pharmaceutical compositions can also be prepared containing another compound of the formula I or a salt thereof according to one of the preceding preparation examples.

What is claimed is:

1. A 1-acyl-4-aliphatylaminopiperidine compound of the formula I

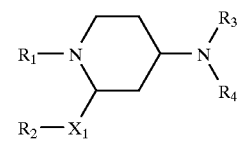

in which $R_1$ is a benzoyl, naphthoyl or cycloalkanoyl radical which is unsubstituted or substituted by lower alkyl, lower alkoxy, halogen and/or trifluoromethyl;

$R_2$ is cycloalkyl or a phenyl or haphthyl radical which is unsubstituted or substituted by lower alkyl, lower alkoxy, halogen, nitro, cyano and/or trifluoromethyl;

$R_3$ and $R_4$ together are lower alkylene or aza-, oxa- or thia-lower alkylene; or $R_3$ is lower alkyl, lower alkoxy-lower alkyl, di-lower alkylamino-lower alkyl or a radical of the formula —(CH$_2$)$_n$—C(=O)—R$_5$ (Ia); and R$_4$ is hyfrogen, lower alkyl or a radical of the formula —(CH$_2$)$_n$—C(=O)—R$_5$ (Ia);

R$_5$ is (I) hydrogen, alkyl or alkyl which is substituted by halogen, lower alkoxy, amino or amino substituted by lower alkyl, amino-lower alkyl, mono-or di-lower alkylaminoalkyl, lower alkanoyl, lower alkoxycarbonyl or lower alkylene or aza-, oxa- or thia-lower alkylene, (ii) hydroxyl, cycloalkoxy, lower alkoxy or lower alkoxy which is substituted by lower alkoxy, amino or amino substituted by lower alkyl, amino-lower alkyl, mono- or di-lower alkylamino-alkyl, lower alkanoyl, lower alkoxycarbonyl or lower alkylene or aza-, oxa- or thia-lower alkylene, or (iii) amino or amino substituted by lower alkyl, cycloalkyl, amino-lower alkyl, mono- or di-lower alkylamino-alkyl, lower alkanoyl, lower alkoxycarbonyl or lower alkylene or aza-, oxa- or thia-lower alkylene;

X$_1$ is methylene, ethylene, a direct bond, a free or ketalized carbonyl group or a free or etherified hydroxymethylene group; and n is 0 or 1, or a salt thereof;

with the proviso that the compound of formula I is not (2R*,4S*)-N-[1-(3,5-bistrifluoromethyl-benzoyl)-2-(4-nitrobenzyl)-piperidin-4-yl]acetamide; (2R,4RS)-N-[2-Benzyl-1-(3,5-dimethylbenzoyl)-4-piperidyl]trifluoroacetamide; (2R*,4S*)-2-(4-Chlorobenzyl)-1-(3,5-dimethylbenzoyl)-N-acetyl-4-piperidinamine; or (2R*,4S*)-N-Acetyl-2(3,4-dichlorobenzyl)-1-(3,5-dimetbylbenzoyl)A-4-piperdinamime.

2. A compound according to claim 1 of the formula I, in which

R$_1$ is a benzoyl, naphthoyl or 3- to 8-membered cycloalkanoyl radical which is unsubstituted or substituted by lower alkyl, lower alkoxy, halogen and/or trifluoromethyl;

R$_2$ is 3- to 8-membered cycloalkyl or a phenyl or naphthyl radical which is unsubstituted or substituted by lower alkyl, lower alkoxy, halogen, nitro, cyano and/or trifluoromethyl;

R$_3$ and R$_4$ together are lower alkylene or aza-, oxa- or thia-lower alkylene; or R$_3$ is lower alkyl, lower alkoxy-lower alkyl, di-lower alkylamino-lower alkyl or a radical of the formula —(CH$_2$)$_n$—C(=O)—R$_5$ (Ia); and R$_4$ is hydrogen, lower alkyl or a radical of the formula —(CH$_2$)$_n$—C(=O)—R$_5$ (Ia);

R$_5$ is (i) hydrogen, C$_1$–C$_{14}$alkyl or C$_1$–C$_{14}$alkyl which is substituted by halogen, lower alkoxy, amino or amino which is substituted by lower alkyl, amino-lower alkyl, mono- or di-lower alkylaminoalkyl, lower alkanoyl, lower alkoxycarbonyl or lower alkylene or 3-aza-, 3-oxa- or 3-thia-C$_4$–C$_6$alkylene, (ii) hydroxyl, 3- to 8-membered cycloalkoxy, lower alkoxy or lower alkoxy, which is substituted by lower alkoxy, amino or amino which is substituted by lower alkyl, amino-lower alkyl, mono- or di-lower alkylaminoalkyl, lower alkanoyl, lower alkoxycarbonyl or lower alkylene or 3-aza-, 3-oxa- or 3-thia-C$_4$–C$_6$alkylene, or (iii) amino or amino which is substituted by lower alkyl, 3- to 8-membered cycloalkyl, amino-lower alkyl, mono- or di-lower alkylaminoalkyl, lower alkanoyl, lower alkoxycarbonyl or lower alkylene or 3-aza-, 3-oxa- or 3-thia-C$_4$–C$_6$alkylene;

X$_1$ is methylene, ethylene, a direct bond, a carbonyl group, di-lower alkoxymethylene, hydroxymethylene or lower alkoxymethylene; and n is 0 or 1;

or a salt thereof.

3. A compound according to claim 1 of the formula I, in which

R$_1$ is a benzoyl or naphthoyl radical which is unsubstituted or substituted by lower alkyl, lower alkoxy, halogen and/or trifluoromethyl;

R$_2$ is 5- to 7-membered cycloalkyl or a phenyl or naphthyl radical which is unsubstituted or substituted by lower alkyl, lower alkoxy, halogen, nitro, cyano and/or trifluoromethyl;

R$_3$ and R$_4$ together are C$_4$–C$_6$alkylene or 3-aza-, 3-oxa- or 3-thia-C$_4$–C$_6$alkylene, in particular 3-aza-, 3-oxa- or 3-thiapentylene, or R$_3$ is lower alkyl, lower alkoxy-lower alkyl, di-lower alkylamino-lower alkyl or a radical of the formula —(CH$_2$)$_n$—C(=O)—R$_5$ (Ia); and R$_4$ is hydrogen, lower alkyl or a radical of the formula —(CH$_2$)$_n$—C(=O)—R$_5$ (Ia);

R$_5$ is (i) hydrogen, C$_1$–C$_{14}$alkyl or C$_1$–C$_{14}$alkyl, which is substituted by halogen, lower alkoxy, amino or amino which is substituted by lower alkyl, amino-lower alkyl, mono- or di-lower alkylaminoalkyl, lower alkanoyl, lower alkoxycarbonyl or C$_4$–C$_6$alkylene or 3-aza-, 3-oxa- or 3-thia-C$_4$–C$_6$alkylene, in particular 3-aza-, 3-oxa- or 3-thiapentylene, (ii) hydroxyl, 3- to 8-membered cycloalkoxy, lower alkoxy or lower alkoxy which is substituted by lower alkoxy, amino or amino which is substituted by lower alkyl, amino-lower alkyl, mono- or di-lower alkylaminoalkyl, lower alkanoyl, lower alkoxycarbonyl or C$_4$–C$_6$alkylene or 3-aza-, 3-oxa- or 3-thia-C$_4$–C$_6$alkylene, in particular 3-aza-, 3-oxa- or 3-thiapentylene, or (iii) amino or amino which is substituted by lower alkyl, C$_5$–C$_7$cycloalkyl, amino-lower alkyl, mono- or di-lower alkylaminoalkyl, lower alkanoyl, lower alkoxycarbonyl or C$_4$–C$_6$alkylene or 3-aza-, 3-oxa- or 3-thia-C$_4$–C$_6$alkylene, in particular 3-aza-, 3-oxa- or 3-thiapentylene;

X$_1$ is methylene, ethylene, a direct bond, a carbonyl group, di-lower alkoxymethylene, hydroxymethylene or lower alkoxymethylene; and n is 0 or 1;

or a salt thereof.

4. A compound according to claim 1 of the formula I, in which

R$_1$ is benzoyl or benzoyl which is substituted by lower alkyl, lower alkoxy, halogen and/or trifluoromethyl;

R$_2$ is phenyl, phenyl which is substituted by lower alkyl, lower alkoxy, halogen, nitro, cyano and or trifluoromethyl, or naphthyl;

R$_3$ and R$_4$ together are C$_4$–C$_6$alkylene; or

R$_3$ is lower alkyl, di-lower alkylamino-lower alkyl or a radical of the formula —(CH$_2$)$_n$—C(=O)—R$_5$ (Ia); and R$_4$ is hydrogen, lower alkyl or a radical of the formula —(CH$_2$)$_n$—C(=O)—R$_5$(1a);

R$_5$ is (i) hydrogen, lower alkyl or halo-lower alkyl; (ii) hydroxyl, C$_4$–C$_6$cycloalkoxy, lower alkoxy, lower alkoxy-lower alkoxy or di-lower alkylamino-lower alkoxy, or (iii) amino, lower alkylamino, di-lower alkylamino, C$_5$–C$_7$cycloalkylamino or di-lower alkylamino-lower alkylamino;

X$_1$ is methylene; and n is 0 or 1;

or a salt thereof.

5. A compound of the formula I, in which $R_1$ is a benzoyl, naphthoyl or cycloalkanoyl radical which is unsubstituted or substituted by $C_1$–$C_4$alkyl, $C_1$–$C_4$alkoxy, halogen, and/or trifluoromethyl, $R_2$ is phenyl which is unsubstituted or substituted by $C_1$–$C_4$alkyl, $C_1$–$C_4$alkoxy, halogen, nitro, cyano and/or trifluoromethyl, or unsubstituted naphthyl, $R_3$ is $C_3$–$C_7$alkyl, $C_1$–$C_4$alkoxycarbonyl-$C_1$–$C_4$alkyl, $C_1$–$C_4$alkoxy-$C_2$–$C_4$alkoxycarbonyl-$C_1$–$C_4$alkyl, 5- to 7-membered cycloalkoxycarbonyl-$C_1$–$C_4$alkyl, carbamoyl-$C_1$–$C_4$alkyl, N—$C_1$–$C_4$alkylcarbamoyl-$C_1$–$C_4$alkyl, N,N-di-$C_1$–$C_4$alkylcarbamoyl-$C_1$–$C_4$alkyl, N—$C_1$–$C_4$alkylamino-$C_1$–$C_4$alkyl, $C_1$–$C_7$alkanoyl, trihalo-$C_1$–$C_7$alkanoyl, amino-$C_1$–$C_7$alkanoyl, N—$C_1$–$C_4$alkylamino-$C_1$–$C_4$alkanoyl, N,N-di-$C_1$–$C_4$alkylamino-$C_1$–$C_4$alkanoyl, morpholino-$C_1$–$C_7$alkanoyl, $C_1$–$C_7$alkanoylamino-$C_1$–$C_4$alkanoyl, $C_1$–$C_4$alkoxycarbonyl, or N,N-di-$C_1$–$C_4$alkylamino-$C_2$–$C_4$alkoxycarbonyl, and $R_4$ is hydrogen or $C_1$–$C_4$alkoxycarbonyl-$C_1$–$C_4$alkyl, $C_1$–$C_4$alkoxy-$C_2$–$C_4$alkoxycarbonyl-$C_1$–$C_4$alkyl, 5- to 7-membered cycloalkoxycarbonyl-$C_1$–$C_4$alkyl, carbamoyl-$C_1$–$C_4$alkyl, N—$C_1$–$C_4$alkylcarbamoyl-$C_1$–$C_4$alkyl, N,N-di-$C_1$–$C_4$alkylcarbamoyl-$C_1$–$C_4$alkyl, N—$C_1$–$C_4$alkylamino-$C_1$–$C_4$alkyl, or $R_3$ and $R_4$, together with the N atom bonding them, are morpholino and $X_1$ is methylene, or a salt thereof.

6. A compound according to claim 1 of the formula I, in which $R_1$ is benzoyl or benzoyl which is substituted by lower alkyl, lower alkoxy, halogen and/or trifluoromethyl;

$R_2$ is phenyl, phenyl which is substituted by lower alkyl, lower alkoxy, halogen, nitro, cyano and/or trifluoromethyl, or naphthyl;

$R_3$ and $R_4$ together are $C_4$–$C_6$alkylene; or $R_3$ is lower alkyl, di-lower alkylamino-lower alkyl or a radical of the formula —$(CH_2)_n$—C(=O)—$R_5$ (Ia); and $R_4$ is hydrogen;

$R_5$ is (i) hydrogen, lower alkyl or halo-lower alkyl; (ii) hydroxyl, $C_4$–$C_6$cycloalkoxy, lower alkoxy, lower alkoxy-lower alkoxy or di-lower alkylamino-lower alkoxy, or (iii) amino, lower alkylamino, di-lower alkylamino, $C_5$–$C_7$cycloalkylamino or di-lower alkylamino-lower alkylamino;

$X_1$ is methylene; and n is 0 or 1;

or a salt thereof.

7. A compound according to claim 1 of the formula I, in which $R_1$ is benzoyl which is disubstituted by $C_1$–$C_4$alkyl, $C_1$–$C_4$alkoxy, halogen and/or trifluoromethyl;

$R_2$ is phenyl, phenyl which is substituted by $C_1$–$C_4$alkyl, $C_1$–$C_4$alkoxy, halogen, nitro, cyano and/or trifluoromethyl, or naphthyl;

(i) $R_5$ is a radical of the formula —$(CH_2)_n$—C(=O)—$R_5$ (Ia); $R_4$ is hydrogen; n is 0 and $R_5$ is $C_1$–$C_7$alkyl, $C_5$–$C_7$cycloalklamino or di-$C_1$–$C_4$alkylamino-$C_2$–$C_4$alkoxy; or (ii) $R_3$ is a radical of the formula —$(CH_2)_n$—C(=O)—$R_5$ (Ia); $R_4$ is hydrogen; n is 1; and $R_5$ is amino; and $X_1$ is methylene;

or a salt thereof.

8. A compound according to claim 1 of the formula I, in which $R_1$ is benzoyl which is disubstituted by trifluoromethyl;

$R_2$ is phenyl or phenyl which is substituted by halogen;

$R_3$ is a radical of the formula —$(CH_2)_n$—C(=O)—$R_5$ (Ia);

$R_4$ is hydrogen;

$R_5$ is $C_1$–$C_7$alkyl, $C_5$–$C_7$cycloalkylamino or di-$C_1$–$C_4$alkylamino-$C_2$–$C_4$alkoxy;

n is 0; and $X_1$ is methylene;

or a salt thereof.

9. A compound according to claim 1 of the formula I, in which $R_1$ is 3,5-bistrifluoromethylbenzoyl;

$R_2$ is phenyl or phenyl which is substituted by halogen;

$R_3$ is a radical of the formula —$(CH_2)_n$—C(=O)—$R_5$ (Ia);

$R_4$ is hydrogen; n is 0;

$R_5$ is $C_1$–$C_4$alkyl, or $C_5$–$C_7$cycloalkylamino; and $X_1$ is methylene;

or a salt thereof.

10. A compound according to claim 1 of the formula I, in which the C atom to which the group —$X_1$—$R_2$ is bonded (essentially) has the R configuration and the C atom to which the group —N($R_3$)($R_4$) is bonded (essentially) has the S configuration according to Cahn-lngold-Prelog.

11. A compound according to claim 1 selected from the group consisting of:

(2R,4S)-2-[2-Benzyl-1-(3,5-bistrifluoromethylbenzoyl)piperidin-4-ylamino]acetamide;

methyl (2R,4S)-2-[2-benzyl-1-(3,5-bistrifluoromethylbenzoyl)piperidin-4-ylamino]acetate;

methyl (2R,4S)-2-{[2-benzyl-1-(3,5-bistrifluoromethylbenzoyl)piperidin-4-yl]-methoxycarbonylmethylamino}acetate;

(2R,4S)-2-[2-benzyl-1-(3,5-bistrifluoromethylbenzoyl)piperidin-4-ylamino]acetamide (2R,4S)-2-{[2-benzyl-1-(3,5-bistrifluoromethylbenzoyl)piperidin-4-yl]carbamoylmethyl-amino}acetamide;

(2R,4S)-2-[2-benzyl-1-(3,5-bistrifluoromethylbenzoyl)piperidin-4-ylamino]acetic acid;

(2R,4S)-2-[2-benzyl-1-(3,5-bistrifluoromethylbenzoyl)piperidin-4-ylaminol-N-(2-dimethyl-aminoethyl)acetamide;

tert-butyl (2R,4S)-N-{[2-benzyl-1-(3,5-bistrifluoromethylbenzoyl)piperidin-4-ylcarbamoyl]methyl}carbamate;

(2R,4S)-2-amino-N-[2-benzyl-1-(3,5-bistrifluoromethylbenzoyl)piperidin-4-yl]acetamide;

tert-butyl (2R,4S)-2-2-benzyl-1-(3,5-bistdfluoromethylbenzoyl)piperidin-4-ylamino]acetate;

tert-butyl (2R,4S)-2-{[2-benzyl-1-(3,5-bistrifluoromethylbenzoyl)piperidin-4-yl]-tert-butoxycarbonylmethylamino}acetate;

isopropyl (2R,4S)-2-[2-benzyl-1-(3,5-bistrifluoromethylbenzoyl)piperidin-4-ylamino]acetate;

isopropyl (2R,4S)-2-([2-benzyl-1-(3,5-bistrifluoromethylbenzoyl)piperidin-4-yl]-isopropoxycarbonylmethylamino}acetate;

(2R,4S)-2-[2-benzyl-1-(3,5-bistrifluoromethylbenzoyl)
piperidin-4-ylamino]-N-isopropylacetamide;

(2R,4S)-2-[[2-benzyl-1-(3,5-bistrfluoromethylbenzoyl)
piperdin-4-yl]-(N-isopropylcarbamoylmethyl)amino]-
N-isopropylacetamide;

ethoxyethyl (2R,4S)-2-[2-benzyl-1-(3,5-
bistrifluoromethylbenzoyl)piperidin-4-ylamino]
acetate;

2-ethoxyethyl (2R,4S)-N-[[2-benzyl-1-(3,5-
bistdfluoromethylbenzoyl)piperidin-4-yl]-(N-(2-
ethoxyethoxycarbonylmethyl))amino]acetate;

(2R,4S)-N-[2-benzyl-1-(3,5-bistrifluoromethylbenzoyl)
piperidin-4-yl]-2-(dimethylamino)-acetamide;

(2R,4S)-2-[2-benzyl-1-(3,5-bistrifluoromethylbenzoyl)
piperidin-4-ylamino)-N,N-dimethylacetamide;

(2R,4S)-2-{[2-benzyl-1-(3,5-bistrifluoromethylbenzoyl)
piperidin-4-yl]dimethyl-carbamoylmethylamino}-N,
N-dimethylacetamide;

(2R,4S)-N-[2-benzyl-1-(3,5-bistrifluoromethylbenzoyl)
piperidin-4-yI]-2-(morpholin-4-yl)-acetamide;

cyclohexyl(2R,4S)-2-[2-benzyl-1-(3,5-
bistdfluoromethylbenzoyl)piperidin-4-ylamino]
acetate;

cyclohexyl(2R,4S)-2-{[2-benzyl-1-(3,5-
bistrifluoromethylbenzoyl)piperidin-4-yl]-N-
(cyclohexyloxycarbonylmethyl)amino}acetate;

(2R,4S)-4-amino-2-benzyl-1-(3,5-
bistrifluoromethylbenzoyl)-N-(3-
dimethylaminopropyl)-piperidine dihydrochloride;

3-dimethylaminopropyl (2R,4S)-N-[2-benzyl-1-(3,5-
bistriluoromethylbenzoyl)piperidin-4-yl]-carbamate;

(2R,4S)-2-benzyl-1-(3,5-bistrifluoromethylbenzoyl)-4-
morpholin-4-yl-piperidine;

(2R,4S)-4-amino-2-benzyl-1-(3,5-
bistrifluoromethylbenzoyl)-N-isobutylpiperidine;

isobutyl (2R,4S)-N-[2-benzyl-1-(3,5-
bistriluoromethylbenzoyl)piperidin-4-yl)carbamate;

(2R,4S)-4-amino-2-benzyl-1-(3,5-
bistrifluoromethylbenzoyl)-N-(2,2-dimethylpropyl)
piperidine;

2-methoxyethyl (2R,4S)-2-[2-benzyl-1-(3,5-
bistriluoromethylbenzoyl)piperidin-4-ylamino]-
acetate;

2-methoxyethyl (2R,4S)-{2-benzyl-1-(3,5-
bistrifluoromethylbenzoyl)piperidin-4-yl]-N-(2-
methoxyethoxycarbonylmethyl)amino]acetate;

2-dimethylaminoethyl (2R,4S)-N-[2-benzyl-1-(3,5-
bistrifluoromethylbenzoyl)piperidin-4-yl]-carbamate;

(2R,4S)-N-[2-benzyl-1-(3,5-bistrifluoromethylbenzoyl)
pipendin-4-yl]acetamide;

(2R,4S)-N-[2-benzyl-1-(3,5-dimethylbenzoyl)piperidin-
4-yl]butyramide;

(2R,4S)-N-[2-benzyl-1-(3,5-dichIorobenzoyl)piperidin-
4-yl]butyramide;

(2R,4S)-N-[1-(3,5-bistrifluoromethylbenzoyl)-2-(4-
chlorobenzyl)pipen'din-4-yl]formamide;

(2R,4S)-N-[1-(3,5-bistrifluoromethylbenzoyl)-2-(4-
chlorobenzyl)piperidin-4-yl]acetamide;

(2R,4S)-N-[1-(3,5-bistrifluoromethylbenzoyl)-2-(4-
chlorobenzyl)piperidin-4-yl]propionamide;

(2R,4S)-N-[1-(3,5-bistriluoromethylbenzoyl)-2-(4-
chlorobenzyl)piperidin-4-yl]butyramide;

N-[2-benzyl-1-(3,5-dimethylbenzoyl)piperidin-4-yl]-2,2,
2-trifluoroacetamide;

(2R,4S)-2-acetylamino-N-[1-(3,5-
bistrifluoromethylbenzoyl)-2-(4-chlorobenzyl)
piperidin-4-yl]-acetamide;

isobutyl (2R,4S)-N-[1-(3,5-bistrifluoromethylbenzoyl)-2-
(4-chlorobenzyl)piperdin-4-yl]-carbamate;

(2R,4S)-2-[1-(3,5-bistriluoromethylbenzoyl)-2-(4-
chlorobenzyl)piperidin-4-ylamino]-acetamide;

(2R,4S)-2-{[1-(3,5-bistrifluoromethylbenzoyl)-2-(4-
chlorobenzyl)piperidin-4-yl]-N-carbamoyl-
methylamino}acetamide;

(2R*,4S*)-N-[1-(3,5-dimethylbenzoyl)-2-(4-nitrobenzyl)
piperidin-4-yl]acetamide;

(2R*,4S*)-N-[1-(3,5-dimethylbenzoyl)-2-(4-
cyanobenzyl)piperidin-4-yl]acetamide;

(2R*,4S*)-N-[1-(3,5-bistrifluoromethylbenzoyl)-2-(4-
cyanobenzyl)piperidin-4-yl]acetamide;

(2R*,4S*)-N-[1-(3,5-dichlorobenzoyl)-2-(4-
chlorobenzyl)piperidin-4-yl]acetamide;

(2R*,4S*)-N-[1-(3,5-dimethylbenzoyl)-2-(4-
methoxybenzyl)piperidin-4-yl]acetamide;

(2R*,4S*)-N-[1-(3,5-bistriluoromethylbenzoyl)-2-(3-
methoxybenzyl)piperidin-4-yl]acetamide;

(2R*,4S*)-N-[1-(3,5-dimethylbenzoyl)-2-(4-
triuoromethylbenzyl)piperidin-4-yl]acetamide;

(2R*,4S*)-N-[1-(3,5-dimethylbenzoyl)-2-(2,4-
dichlorobenzyl)piperidin-4-yl]acetamide;

(2R*,4S*)-N-[ 1-(3,5-dimethylbenzoyl)-2-(2-naphthyl)
piperidin-4-yl]acetamide and (2R*,4S*)-N-[1-(3,5-dimethylbenzoyl)-2-(4-iodobenzyl)
piperidin-4-yl]acetamide;

or in each case a pharmaceutically acceptable salt thereof.

12. A compound according to claim 1 selected from the group consisting of:

(2R,4S)-N-[1-(3,5-Bistrifluoromethylbenzoyl)-2-(4-
chlorobenzyl)piperldin-4-yl]-pentanamide;

(2R,4S)-1-[1-(3,5-bistrifluoromethylbenzoyl)-2-(4-
chlorobenzyl)pipe1din-4-yl]-3-tert-butylurea;

(2R,4S)-1-[1-(3,5-bistrifuoromethylbenzoyl)-2-(4-
chlorobenzyl)piperdin-4-yl]-3-isprolurea;

(2R,4S)-1-[1-(3,5-bistrifluoromethylbenzoyl)-2-(4-
chlorobenzyl)piperidin-4-yl-3-ethylurea;

(2R,4S)-1-[1-(3,5-bistriluoromethylbenzoyl)-2-(4-
chlorobenzyl)piperidin-4-yl]-3-cyclohexylurea;

(2R,4S)-1[1-(3,5-bistrifluoromethylbenzoyl)-2-(4-
chlorobenzyl)pipeadin-4-yl]-3-propylurea;

(2R,4S)-1-[2-benzyl-1-(3,5-bistrifluoromethylbenzoyl)
piperidin-4-yl]-3-cyclohexylurea;

(2R,4S)-1-[2-benzyl-1-(3,5-bistrifluoromethylbenzoyl)
piperidin-4-yl]-3-tert-butylurea;

(2R,4S)-1-[2-benzyl-1-(3,5-bistriluoromethylbenzoyl)
piperidin-4-yl]-3-isopropylurea;

n-octyl (2R,4S)-2-[2-benzyl-1-(3,5-
bistrifluoromethylbenzoyl)piperidin-4-ylamino]acetate
and n-octyl (2R,4S)-2-{2-benzyl-1-(3,5-
bistrifluoromethylbenzoyl)piperidin-4-yl]
methoxycarbonyl-methylamino}acetate;

n-decyl (2R,4S)-2-[2-benzyl-1-(3,5-
bistrifluoromethylbenzoyl)piperidin-4-ylamino]acetate
and n-decyl (2R,-4S)-2-([2-benzyl-1-(3,5-bistrifluoromethylbenzoyl)piperidin-4-yl]methoxy-carbonylmethylamino}acetate;

n-dodecyl (2R,4S)-2-[2-benzyl-1-(3,5-bistrifluoromethylbenzoyl)piperidin-4-ylamino]acetate and n-dodecyl (2R,4S)-2-{[2-benzyl-1-(3,5-bistrifluoromethylbenzoyl)piperidin-4-yl]methoxy-carbonylmethylamino}acetate or in each case a pharmaceutically acceptable salt thereof.

13. A pharmaceutical composition containing a therapeutically effective amount of a compound according to claim 1, including the compound (2R*,4S*)-N-[1-(3,5-bistrifluoromethylbenzoyl)-2-(4-nitrobenzyl)piperidin-4-yl] acetamide, or a pharmaceutically acceptable salt thereof, in addition to customary pharmaceutical excipients and carriers.

14. A process for the preparation of a compound of the formula I according to claim 1, wherein
a) the radical $R_1$ is introduced into a compound of the formula II

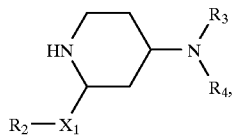

(II)

in which $R_2$, $R_3$, $R_4$ and $X_1$ are as defined, or b) compounds of the formulae III

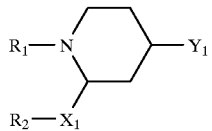

(III)

and $Y_2$—$R_3$ (IV), in which $Y_1$ is a group of the formula —N($R_4$)—H and $Y_2$ is hydroxyl, reactive esterified hydroxyl or, if $R_3$ is a radical of the formula —(CH$_2$)$_n$—C(=O)—$R_5$ (Ia) and n is 0, is etherified hydroxyl or $Y_1$ is free or reactive esterified hydroxyl and $Y_2$ is a group of the formula —N($R_4$)—H, $R_1$, $R_2$, $R_3$, $R_4$ and $X_1$ being as defined, or their salts are condensed with one another or c) for the preparation of compounds of the formula I, in which $R_4$ is hydrogen, the group $Y_3$ is removed from a compound of the formula V

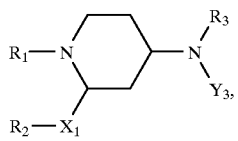

(V)

in which $Y_3$ is an amino protective group and $R_1$, $R_2$, $R_3$ and $X_1$ are as defined, or from a salt thereof or d) for the preparation of compounds of the formula I, in which $R_3$ is lower alkyl, di-lower alkylamino-lower alkyl or lower alkoxy-lower alkyl and $R_4$ is hydrogen or lower alkyl, a compound of the formula VI

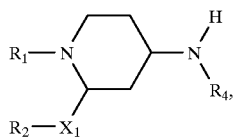

(VI)

in which $R_1$, $R_2$, $R_4$ and $X_1$ are as defined, or a salt thereof is reacted under reducing conditions with an appropriate aldehyde of the formula O=CH—R (VII) or e) for the preparation of compounds of the formula I, in which $R_3$ and $R_4$ together are lower alkylene or aza-, oxa- or thia-lower alkylene, a compound of the formula VIII

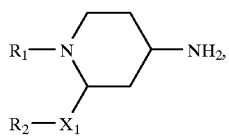

(VIII)

in which $R_1$, $R_2$ and $X_1$ are as defined, or a salt thereof is condensed with a reactive diester of an appropriate lower alkanediol or aza-, oxa- or thia-lower alkanediol or f) for the preparation of compounds of the formula I, in which $X_1$ is a carbonyl or hydroxymethylene group, compounds of the formulae IX

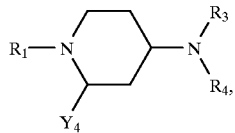

(IX)

and $Y_5$—$R_2$ (X), in which one of the radicals $Y_4$ and $Y_5$ is formyl or a carboxyl group which is free, converted into an anhydride or esterified, and the other is a metallic radical and $R_2$, $R_3$ and $R_4$ are as defined, are condensed with one another and, if desired, a compound which is obtained is converted into another compound of the formula I, an isomer mixture obtainable according to the process is separated into the components and the preferred isomer is in each case separated off and/or a free compound obtainable according to the process is converted into a salt or a salt obtainable according to the process is converted into the corresponding free compound.

15. A method for the treatment of the human or animal body comprising administering a therapeutically effective amount of a compound selected from the group consisting of the compound of claim 1, (2R,4RS)-N-[2-Benzyl-1-(3,5-dimethylbenzoyl)-4-piperidyl]trifluoroacetamide, (2R*, 4S*)-2-(4–Chlorobenzyl)-1-(3,5-dimethylbenzoyl)-N-acetyl-4-piperidinamine, and (2R*,4S*)-N-Acetyl-2-(3,4-dichlorobenzyl)-1-(3,5-dimethylbenzoyl)-4-piperidinamine.

16. A method for the treatment of disorders which are induced by substance P comprising administering a therapeutically effective amount of a compound selected from the group consisting of the compound of claim 1, (2R,4RS)-N-[2-Benzyl-1-(3,5-dimethylbenzoyl)-4-piperidyl] trifluoroacetamide, (2R*,4S*)-2-(4-Chlorobenzyl)-1-(3,5-dimethylbenzoyl)-N-acetyl-4-piperidinamine, and (2R*, 4S*)-N-Acetyl-2-(3,4-dichlorobenzyl)-1-(3,5-dimethylbenzoyl)-4-piperidinamine.

* * * * *

UNITED STATES PATENT AND TRADEMARK OFFICE
CERTIFICATE OF CORRECTION

PATENT NO. : 5,935,951
DATED : August 10, 1999
INVENTOR(S) : Silvio Ofner, et al.

It is certified that error appears in the above-identified patent and that said Letters Patent is hereby corrected as shown below:

Column 52, claim 11, line 25, should read:

-- (2R*,4S*)-N-[1-(3,5-bistrifluoromethylbenzoyl)-2-(3- --

Column 52, claim 11, line 28, should read:

-- trifluoromethylbenzyl)piperidin-4-yl]acetamide; --.

Column 52, claim 12, line 42, should read:

-- chlorobenzyl)piperidin -4-yl]-3-tert- butylurea; --.

Column 52, claim 12, line 45, should read:

-- chlorobenzyl)piperidin-4-yl]-3-isopropylurea; --.

Column 52, claim 12, line 48, should read:

-- (2R,4S)-1-[1-(3,5-bistrifluoromethylbenzoyl)-2-(4- --.

Column 52, claim 12, line 51, should read:

-- chlorobenzyl)piperidin-4-yl]-3-propylurea; --.

UNITED STATES PATENT AND TRADEMARK OFFICE
CERTIFICATE OF CORRECTION

PATENT NO. : 5,935,951
DATED : August 10, 1999
INVENTOR(S) : Silvio Ofner, et al.

Page 2 of 3

It is certified that error appears in the above-identified patent and that said Letters Patent is hereby corrected as shown below:

Column 48, claim 4, line 52, should read:

-- lower alkoxy, halogen, nitro, cyano and/or --.

Column 51, claim 11, line 45, should read:

-- bistrifluoromethylbenzoyl)piperidin-4-ylamino]- --.

Column 51, claim 11, line 57, should read:

-- (2R,4S)-N-[2-benzyl-1-(3,5-dichlorobenzoyl)piperidin- --.

Column 51, claim 11, line 59, should read:

-- chlorobenzyl)piperidin-4-yl]formamide --.

Column 52, claim 11, line 9, should read:

-- (2R,4S)-2-[1-(3,5-bistrifluoromethylbenzoyl)-2-(4- --.

UNITED STATES PATENT AND TRADEMARK OFFICE
CERTIFICATE OF CORRECTION

PATENT NO. : 5,935,951
DATED : August 10, 1999
INVENTOR(S) : Silvio Ofner, et al.

It is certified that error appears in the above-identified patent and that said Letters Patent is hereby corrected as shown below:

Column 52, Claim 12, line 56 should read:

-- (2R,4S)-1-[2-benzyl-1-(3,5-bistrifluoromethylbenzoyl) --.

Signed and Sealed this

Eleventh Day of July, 2000

Q. TODD DICKINSON

*Attest:*

*Attesting Officer*  *Director of Patents and Trademarks*